US010736598B2

(12) United States Patent
Nagae et al.

(10) Patent No.: US 10,736,598 B2
(45) Date of Patent: Aug. 11, 2020

(54) IMAGE PROCESSING APPARATUS, X-RAY DIAGNOSTIC APPARATUS, AND IMAGE PROCESSING METHOD

(71) Applicant: Canon Medical Systems Corporation, Otawara-shi (JP)

(72) Inventors: Ryoichi Nagae, Nasushiobara (JP); Masahiro Ozawa, Sakura (JP); Yuichiro Watanabe, Yaita (JP)

(73) Assignee: Canon Medical Systems Corporation, Otawara-shi (JP)

( * ) Notice: Subject to any disclaimer, the term of this patent is extended or adjusted under 35 U.S.C. 154(b) by 116 days.

(21) Appl. No.: 15/942,778

(22) Filed: Apr. 2, 2018

(65) Prior Publication Data
US 2018/0279986 A1    Oct. 4, 2018

(30) Foreign Application Priority Data

Mar. 31, 2017   (JP) .................................. 2017-071791

(51) Int. Cl.
*A61B 6/00* (2006.01)
*A61B 6/06* (2006.01)

(52) U.S. Cl.
CPC ............... *A61B 6/547* (2013.01); *A61B 6/06* (2013.01); *A61B 6/4441* (2013.01); *A61B 6/465* (2013.01); *A61B 6/469* (2013.01); *A61B 6/487* (2013.01); *A61B 6/503* (2013.01); *A61B 6/504* (2013.01); *A61B 6/5205* (2013.01); *A61B 6/5217* (2013.01); *A61B 6/5258* (2013.01)

(58) Field of Classification Search
CPC ......... A61B 6/547; A61B 6/06; A61B 6/4441; A61B 6/465; A61B 6/469; A61B 6/487; A61B 6/503; A61B 6/504; A61B 6/5205; A61B 6/5217; A61B 6/5258
See application file for complete search history.

(56) References Cited

U.S. PATENT DOCUMENTS

| 7,792,342 | B2 | 9/2010 | Barbu et al. |
| 9,082,158 | B2 | 7/2015 | Chen et al. |
| 9,119,573 | B2 | 9/2015 | Lu et al. |
| 2010/0104167 | A1 | 4/2010 | Sakaguchi et al. |
| 2014/0051991 | A1 | 2/2014 | Sakaguchi et al. |

(Continued)

FOREIGN PATENT DOCUMENTS

| JP | 2010-131371 | 6/2010 |
| JP | 2014-083230 | 5/2014 |

(Continued)

*Primary Examiner* — Leon Flores
(74) *Attorney, Agent, or Firm* — Oblon, McClelland, Maier & Neustadt, L.L.P.

(57) ABSTRACT

An image processing apparatus according to an embodiment includes processing circuitry. The processing circuitry extracts a fixed object included in chronologically collected X-ray images and having a substantially fixed position. The processing circuitry detects a target object included in each of the X-ray images, on the basis of extraction results of the fixed object. The processing circuitry generates a plurality of corrected images by a correction process to substantially match, with a reference position, the detected position of the target object in an X-ray image other than a reference X-ray image, the reference position being the detected position of the target object in the reference X-ray image.

20 Claims, 12 Drawing Sheets

(56) References Cited

U.S. PATENT DOCUMENTS

| | | | |
|---|---|---|---|
| 2015/0154771 A1 | 6/2015 | Sakaguchi et al. | |
| 2016/0029989 A1* | 2/2016 | Nagae | A61B 6/4482 |
| | | | 378/42 |
| 2016/0029992 A1 | 2/2016 | Iijima et al. | |
| 2017/0065235 A1 | 3/2017 | Sakaguchi et al. | |

FOREIGN PATENT DOCUMENTS

| JP | 2015-128578 | 7/2015 |
|---|---|---|
| JP | 2016-034351 | 3/2016 |
| JP | 2016-034451 | 3/2016 |
| JP | 2016-120144 | 7/2016 |
| JP | 2016-131618 | 7/2016 |

\* cited by examiner

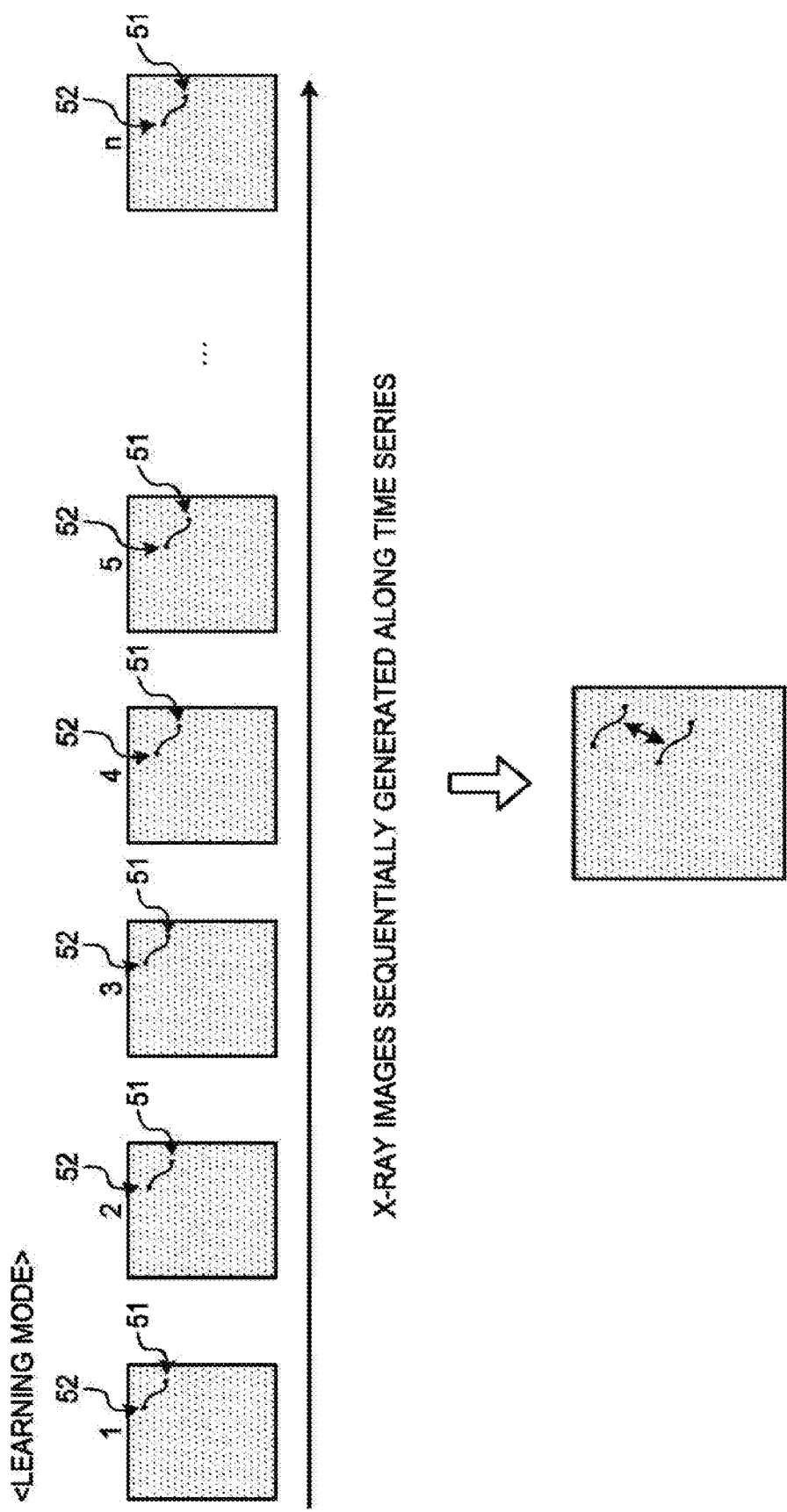

IMAGE PROCESSING APPARATUS, X-RAY DIAGNOSTIC APPARATUS, AND IMAGE PROCESSING METHOD

CROSS-REFERENCE TO RELATED APPLICATIONS

This application is based upon and claims the benefit of priority from Japanese Patent Application No. 2017-71791, filed on Mar. 31, 2017; the entire contents of which are incorporated herein by reference.

FIELD

Embodiments described herein relate generally to an image processing apparatus, an X-ray diagnostic apparatus, and an image processing method.

BACKGROUND

Intravascular intervention treatment is a treatment method of inserting a treatment tool (device) called catheter into a blood vessel, to perform treatment of an affected part generated in the heart, the brain, the liver or the like. For example, in intravascular intervention treatment, the doctor inserts a catheter with a balloon into a narrow segment. Thereafter, for example, the doctor injects liquid into the balloon through the catheter, to expand the balloon. In this manner, the narrow segment is mechanically expanded, and the blood flow is recovered. The catheter with a balloon is extracted out of the body by the doctor, after the liquid in the balloon is absorbed.

In addition, another intravascular intervention treatment using a catheter with a balloon is also performed, to prevent restenosis of the narrow segment expanded with the balloon. In the catheter with a balloon, a metal mesh (stent) is in close contact with the outside of the balloon. In the treatment method, the doctor expands the stent by expanding the balloon, thereafter absorbs the liquid in the balloon, and extracts the catheter out of the body. In this manner, the expanded stent is placed in the narrow segment, to reduce the restenosis rate of the narrow segment.

The intravascular intervention treatment requires movement of the device inserted into the blood vessel to the treatment target region with accuracy. Generally, positioning of the device is performed, with reference to an X-ray image generated and displayed in real time with an X-ray diagnostic apparatus. For this reason, for example, X-ray impermeable metal is attached to two parts (one part in some cases) of the device, as markers indicating the position of the balloon or the stent. The doctor positions the device, with reference to the markers drawn in the X-ray image displayed on the monitor.

However, when intravascular intervention treatment is performed on a blood vessel of an organ that always pulses, such as the heart, or an organ moving with pulsation, the position of the device on the X-ray image always moves. For this reason, positioning the device with reference to the X-ray image becomes a very advanced work for the doctor.

In prior art, a technique of performing moving image display in which the device virtually looks as if the device is stationary is known. In the technique, for example, the marker drawn on sequentially generated X-ray images is tracked, and image transformation is performed such that the position of the marker in each of the X-ray images is the same position as that in the past images. A technique of highlighting the device with high contrast is also known. In the technique, the device is highlighted by, for example, determining an arithmetic mean of images of a plurality of frames in which the position of the marker is corrected to the same position, as a post process.

BRIEF DESCRIPTION OF THE DRAWINGS

FIG. 3 is a diagram for explaining an example of a learning mode according to the first embodiment;

FIG. 6 is a diagram for explaining an example of detection processing with the detection function according to the first embodiment;

DETAILED DESCRIPTION

According to an embodiment, an image processing apparatus includes processing circuitry. The processing circuitry is configured to extract a fixed object included in chronologically collected X-ray images and having a substantially fixed position. The processing circuitry is configured to detect a target object included in each of the X-ray images, on the basis of extraction results of the fixed object. The processing circuitry is configured to generate a plurality of corrected images by a correction process to substantially match, with a reference position, the detected position of the target object in an X-ray image other than a reference X-ray image, the reference position being the detected position of the target object in the reference X-ray image.

The following is a detailed explanation of embodiments of an image processing apparatus and an X-ray diagnostic apparatus, with reference to drawings. The embodiments described hereinafter illustrate X-ray diagnostic apparatuses according to the present application, as an example. The image processing apparatus and the X-ray diagnostic apparatus according to the present application are not limited to the embodiments described hereinafter.

First Embodiment

Figure 1:
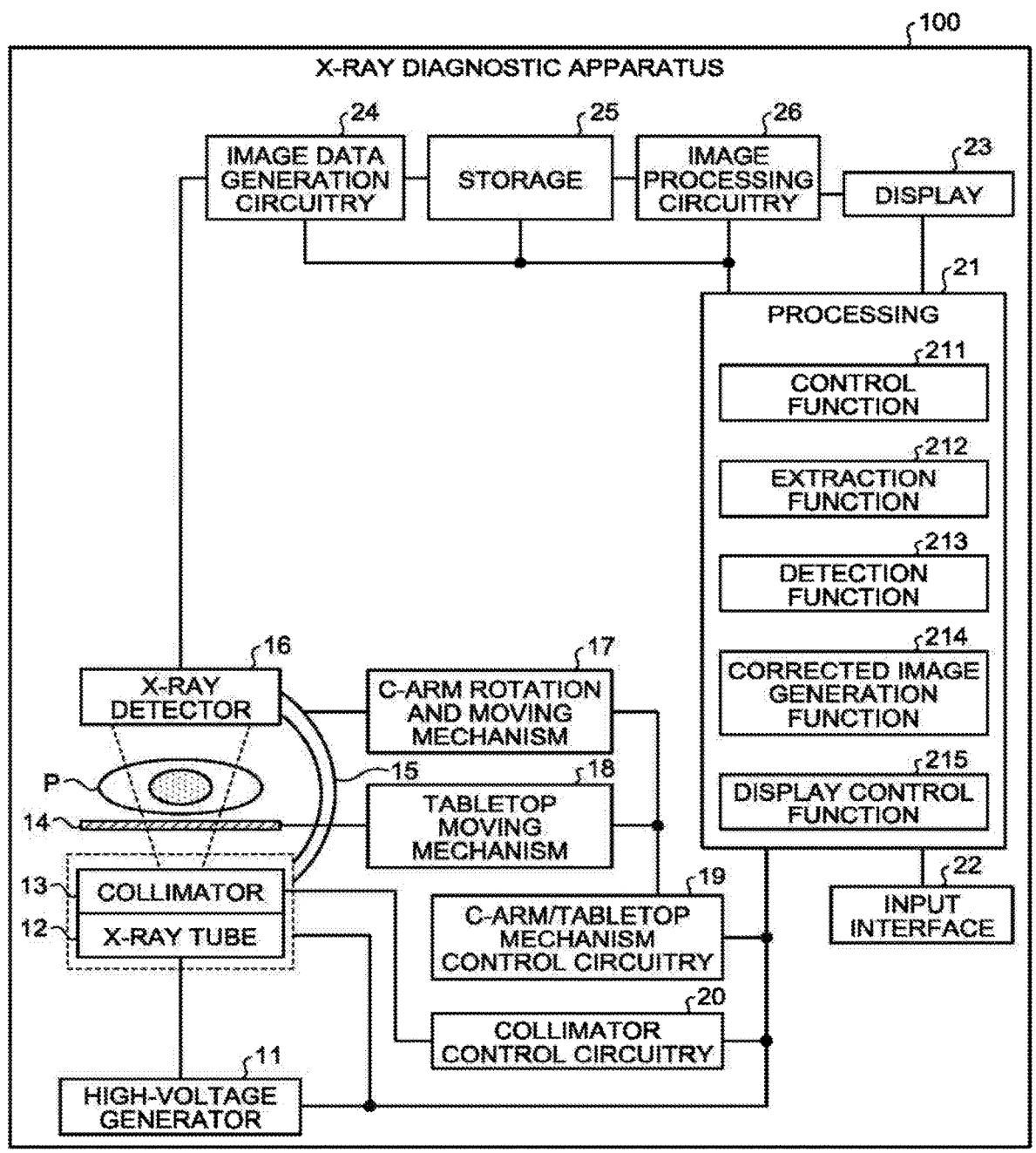
FIG. 1 is a diagram illustrating an example of configuration of an X-ray diagnostic apparatus according to a first embodiment.

First, the following is an explanation of whole configuration of the X-ray diagnostic apparatus according to the first embodiment. FIG. 1 is a diagram illustrating an example of configuration of an X-ray diagnostic apparatus 100 according to the first embodiment. As illustrated in FIG. 1, the X-ray diagnostic apparatus 100 according to the first embodiment includes a high-voltage generator 11, an X-ray tube 12, a collimator 13, a tabletop 14, a C arm 15, an X-ray detector 16, a C-arm rotation and moving mechanism 17, a tabletop moving mechanism 18, C-arm/tabletop mechanism control circuitry 19, collimator control circuitry 20, processing circuitry 21, an input interface 22, a display 23, image data generation circuitry 24, a storage 25, and image processing circuitry 26.

In the X-ray diagnostic apparatus 100 illustrated in FIG. 1, each of the processing functions is stored in the form of a computer program executable with a computer in the storage 25. The C-arm/tabletop mechanism control circuitry 19, the collimator control circuitry 20, the processing circuitry 21, the image data generation circuitry 24, and the image processing circuitry 26 are processors achieving the functions corresponding to respective computer programs by reading and executing the respective computer programs from the storage 25. In other words, the circuits in a state of reading the respective computer programs have respective functions corresponding to the read computer programs.

The term "processor" used in the explanation described above means a circuit, such as a central processing unit (CPU), a graphics processing unit (GPU), an application specific integrated circuit (ASIC), and a programmable logic device (such as a simple programmable logic device (SPLD), a complex programmable logic device (CPLD), and a field programmable gate array (FPGA)). The processor achieves the function by reading and executing a computer program stored in the storage. The apparatus may have a structure of directly installing a computer program in a circuit of the processor, instead of storing the computer program in the storage. In this case, the processor achieves the function by reading and executing the computer program installed in the circuit thereof. Each of the processors in the present embodiment is not limited to the case where each of the processors is configured as a single circuit, but a plurality of independent circuits ay be combined as a processor, to achieve the function.

The high-voltage generator 11 generates a high voltage under the control of the processing circuitry 21, and supplies the generated high voltage to the X-ray tube 12. The X-ray tube 12 generates X-rays using the high voltage supplied from the high-voltage generator 11.

The collimator 13 narrows down the X-rays generated with the X-ray tube 12 such that the X-rays are selectively applied to a region of interest of a subject P, under the control of the collimator control circuitry 20. For example, the collimator 13 includes four slidable collimator blades. The collimator 13 slides these collimator blades, under the control of the collimator control circuitry 20, to narrow down the X-rays generated with the X-ray tube 12 and apply the X-rays to the subject P. The tabletop 14 is a bed on which the subject P is placed, and disposed on a table that is not illustrated. The subject P is not included in the X-ray diagnostic apparatus 100.

The X-ray detector 16 detects the X-rays transmitted through the subject P. For example, the X-ray detector 16 includes detection elements arranged in a matrix manner. Each of the detection elements converts the X-rays transmitted through the subject P into an electric signal, accumulates the electric signals, and transmits the accumulated electric signals to the image data generation circuitry 24.

The C arm 15 holds the X-ray tube 12, the collimator and the X-ray detector 16. The X-ray tube 12 and the collimator 13 are disposed by the C arm 15 to be opposed to the X-ray detector 16, with the subject P interposed between them. FIG. 1 illustrates the case where the X-ray diagnostic apparatus 100 is of a single-plane type, as an example, but the embodiments are not limited thereto. The X-ray diagnostic apparatus 100 may be of a biplane type.

The C-arm rotation and moving mechanism 17 is a mechanism to rotate and move the C arm 15. The C-arm rotation and moving mechanism 17 is also capable of changing a source image receptor distance (SID) serving as a distance between the X-ray tube 12 and the X-ray detector 16. The C-arm rotation and moving mechanism 17 is also capable of rotating the X-ray detector 16 held with the C arm 15. The tabletop moving mechanism 18 is a mechanism to move the tabletop 14.

The C-arm/tabletop mechanism control circuitry 19 controls the C-arm rotation and moving mechanism 17 and the tabletop moving mechanism 18, to regulate rotation and movement of the C arm 15, and movement of the tabletop 14, under the control of the processing circuitry 21. The collimator control circuitry 20 regulates the aperture of the collimator blades of the collimator 13, to control the application range of the X-rays applied to the subject P, under the control of the processing circuitry 21.

The image data generation circuitry 24 generates image data using the electric signals converted from the X-rays with the X-ray detector 16, and stores the generated image data in the storage 25. For example, the image data generation circuitry 24 subjects the electric signal received from the X-ray detector 16 to current/voltage conversion, A (Analog)/D (Digital) conversion, and parallel/serial conversion, to generate image data (projection data). Thereafter, the image data generation circuitry 24 stores the generated image data in the storage 25.

The storage 25 receives the image data generated with the image data generation circuitry 24, and stores the image data therein. The storage 25 also stores computer programs corresponding to various functions and read and executed with the circuits illustrated in FIG. 1 therein. For example, the storage 25 stores therein a computer program corresponding to a control function 211, a computer program corresponding to an extraction function 212, a computer program corresponding to a detection function 213, a computer program corresponding to a corrected image generation function 214, and a computer program corresponding to a display control function 215 that are read and executed with the processing circuitry 21. The storage 25 is an example of the storage.

The image processing circuitry 26 performs various types of image processing on the image data stored in the storage 25, to generate an X-ray image, under the control of the processing circuitry 21 described later. As another example, the image processing circuitry 26 directly acquires image data from the image data generation circuitry 24, and performs various types of image processing on the acquired image data, to generate an X-ray image, under the control of the processing circuitry 21 described later. The image processing circuitry 26 is also capable of storing the X-ray image after image processing in the storage 25. For example, the image processing circuitry 26 is capable of performing various types of processing with image processing filters, such as a moving average (smoothing) filter, a Gaussian filter, a median filter, a recursive filter, and a bandpass filter.

The input interface 22 is achieved with a trackball, a switch button, a mouse, a keyboard, or the like to perform setting of a region (such as a region of interest) and the like, or a foot switch to perform application of X-rays and the like. The input interface 22 is connected with the processing circuitry 21, converts an input operation received from the operator into an electric signal, and outputs the electric signal to the processing circuitry 21. The display 23 displays a graphical user interface (GUI) to receive operator's instructions, and various images generated with the image processing circuitry 26.

The processing circuitry 21 controls operations of the whole X-ray diagnostic apparatus 100. Specifically, the processing circuitry 21 executes various processing, by reading the computer program corresponding to the control function 211 to control the whole apparatus from the storage 25 and executing the computer program. For example, the control function 211 controls the high-voltage generator 11 in accordance with an operator's instruction transferred from the input interface 22, and regulates the voltage supplied to the X-ray tube 12, to control the X-ray quantity applied to the subject P and turning on/off of the X-rays. In addition, for example, the control function 211 controls the C-arm/tabletop mechanism control circuitry 19 in accordance with the operator's instruction, to regulate rotation and movement of the C arm 15 and movement of the tabletop 14. As another example, the control function 211 controls the collimator control circuitry 20 in accordance with the operator's instruction, to regulate the aperture of the collimator blades of the collimator 13, and control the application range of the X-rays applied to the subject P.

The control function 211 also controls image data generation processing with the image data generation circuitry 24, image processing with the image processing circuitry 26, or analysis processing, in accordance with the operator's instruction. The control function 211 also performs control to display the GUI to receive the operator's instruction and the image stored in the storage 25 on the display 23. As illustrated in FIG. 1, the processing circuitry 21 according to the first embodiment executes the extraction function 212, the detection function 213, the corrected image generation function 214, and the display control function 215. The details of the functions will be described later. The image data generation circuitry 24 described above is an example of the acquisition circuitry. The processing circuitry 21 is an example of the processing circuitry.

The whole configuration of the X-ray diagnostic apparatus 100 has been described above. Under the configuration, the X-ray diagnostic apparatus 100 according to the present embodiment enables improvement in image quality. Specifically, the X-ray diagnostic apparatus 100 enables improvement in image quality of the X-ray image in the display of a moving image in which the treatment tool (device) virtually looks as if the device is stationary.

For example, when the doctor performs intravascular intervention treatment using "catheter with a balloon including a stent" on a narrow segment in the heart blood vessel of the subject P, the doctor positions the device with reference to an X-ray image generated and displayed with the X-ray diagnostic apparatus. As described above, when intravascular intervention treatment is performed on the blood vessel of an organ that always pulses, such as the heart, or an organ moving with pulsation, the position of the device on the X-ray image always moves. For this reason, positioning the device with reference to the X-ray image becomes a very advanced work for the doctor.

For this reason, the X-ray diagnostic apparatus 100 tracks, for example, two markers drawn on X-ray images that are sequentially generated, and performs image transformation such that such that the positions of the two markers in each of the X-ray images are the same positions as the past image, to display a moving image in which the device virtually looks as if the device is stationary. For example, the X-ray tube 12 applies X-rays to the region of interest (for example, the heart) of the subject P, and the X-ray detector 16 successively detects the X-rays transmitted through the region of interest. The X-ray diagnostic apparatus 100 performs image processing such that the device included in X-ray images sequentially generated along the time series virtually looks as if the device is stationary or the basis of data successively detected with the X-ray detector 16, to display a moving image in real time.

This structure enables the X-ray diagnostic apparatus 100 to display X-ray images displayed in execution of intravascular intervention treatment executed with reference to X-ray images, with improved visibility of the device, and enables easy positioning of the device. However, the techniques described above may cause erroneous detection of the markers, and deterioration in image quality. For this reason, the X-ray diagnostic apparatus 100 according to the present application improves the accuracy of detection of the markers with the processing circuitry 21 described in detail hereinafter, and enables improvement in image quality in the display of a moving image in which the device virtually looks as if the device is stationary.

First, the following is an explanation of processing in the display of a moving image in which the device virtually looks as if the device is stationary. The following explanation illustrates the case where the processing circuitry 21 performs various functions to control the image processing circuitry 26 to perform the processing, but the processing circuitry 21 may perform the same processing as that of the image processing circuitry 26.

In the case of displaying a moving image in which the device virtually looks as if the device is stationary, the detection function 213 controls the image processing circuitry 26, to specify a certain target object relating to the medical device inserted into the body of the subject P using an image data group sequentially generated with the image data generation circuitry 24 in a predetermined period, and detect the position of the certain target object in a newly generated X-ray image on the basis specified result. Specifically, the detection function 213 controls the image processing circuitry 26 to detect the certain target object included in the X-ray image generated from the image data. It suffices that the predetermined period serving as a target of detection of the target object and the certain target object serving as a target of detection are determined until the point in time when the detection processing is started. For example, they are determined before generation of the image data group, during generation of the image data group, or after generation of the image data group.

For example, the detection function 213 detects coordinates of the stent marker attached to the stent in a new image, whenever a new image serving as a new X-ray image is stored. Specifically, the detection function 213 detects coordinates of the stent marker in X-ray images that are sequentially generated on the basis of information relating to the stent marker drawn on the image. As an example, the detection function 213 detects coordinates of the stent marker in X-ray images that are sequentially generated on the basis of information of the stent marker designated by the operator, or a teacher image of the stent marker.

The detection function 213 generates a plurality of frequency images including a predetermined frequency component from the sequentially generated X-ray images, and detects respective coordinates of the certain target object included in the generated frequency images. Specifically, the detection function 213 generates respective high-frequency images including a high-frequency component from the sequentially generated X-ray images, and detects respective coordinates of the stent marker in the generated high-frequency images. Specifically, the predetermined frequency component is a frequency component including a component corresponding to the certain target object. The detection function 213 generates frequency images in which the certain target object is highlighted, to detect coordinates of the certain target object. It suffices that the predetermined frequency component in the frequency images is determined until the point in time when the detection processing is started. For example, the frequency component is determined before generation of the image data group, during generation of the image data group, or after generation of the image data group.

For example, the detection function 213 performs smoothing processing on the X-ray images, to generate low-frequency images of the X-ray images. The detection function 213 subtracts the low-frequency image from the X-ray image, to generate a high-frequency image obtained by removing the low-frequency image from the X-ray image. In addition, the detection function 213 detects coordinates of the stent marker in the generated high-frequency image. For example, the detection function 213 performs the processing described above on each of the sequentially generated X-ray images, to generate high-frequency images for the respective X-ray images, and detect respective coordinates of the stent marker included in the generated high-frequency images. Generation of the high-frequency images is not limited to the example described above, but may be performed by any method, such as processing using a bandpass filter.

Figure 2A:
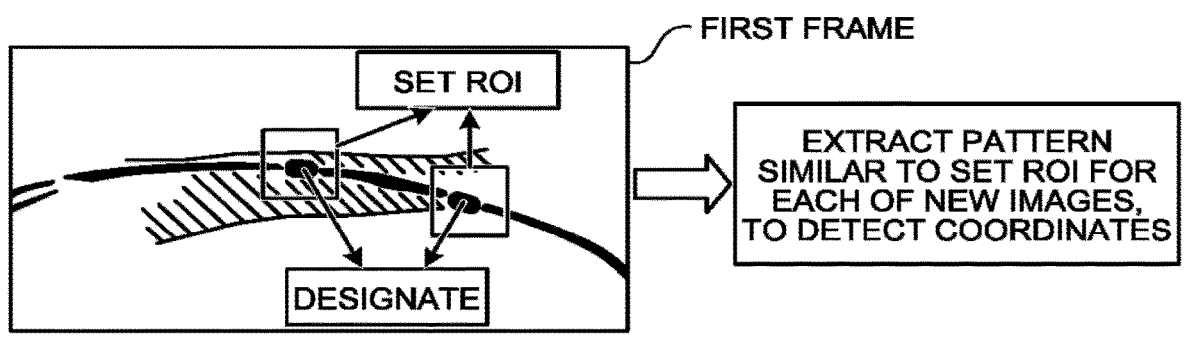
FIG. 2A is a diagram for explaining processing with a detection function according to the first embodiment.
Figure 2B:
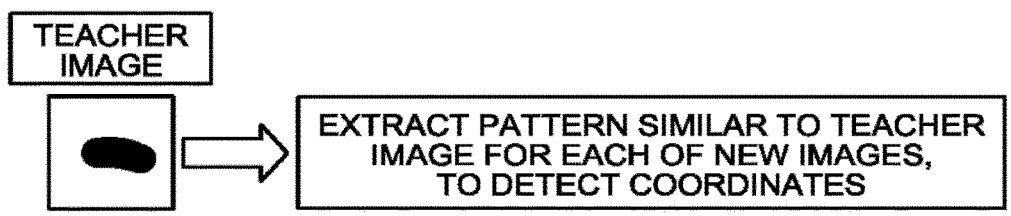
FIG. 2B is a diagram for explaining processing with a detection function according to the first embodiment.

The following is an explanation of processing in the display of a moving image in which the device virtually looks as if the device is stationary, with an example in which coordinates of two stent markers are detected. The following is an explanation of processing after high-frequency images are generated. FIG. 2A and FIG. 2B are diagrams for explaining processing with the detection function 213 according to the first embodiment. For example, the display control function 215 described later performs control display an X-ray image (first frame) generated first and stored in the storage 25 on the display 23, as illustrated in FIG. 2A. The operator (doctor or the like) who has referred to the first frame designates two stent markers in the first frame, through the input interface 22, as illustrated in FIG. 2A. In this manner, the detection function 213 recognizes a display pattern (such as the shapes of the stent markers and luminance information) of the stent markers in the X-ray image, and detects respective coordinates of the two stent markers in the first frame.

Thereafter, as illustrated in FIG. 2A, the detection function 213 sets rectangles with the centers positioned on the respective coordinates of the two stent markers designated in the first frame, as regions of interest (ROI). The detection function 213 extracts patterns similar to the patterns in the set ROIs by, for example, a cross correlation method, for each of sequentially generated new images, and detects the coordinates with the highest cross correlation values as the coordinates of the stent markers.

FIG. 2A illustrates the case where the operator designates two stent markers, but the present embodiment is not limited thereto. The operator may designate one stent marker. In this case, the detection function 213 executes cross correlation using the set ROI from the coordinates of the designated stent marker also in the first frame, to detect coordinates of another stent marker in the first frame.

As another example, the detection function 213 detects coordinates of the stent marker using a teacher image indicating features of the shape and the luminance of the stent marker attached to the stent actually used for treatment in the X-ray image. For example, as illustrated in FIG. 2B, an X-ray image of the stent marker is separately stored as a teacher image. The detection function 213 extracts a pattern similar to the teacher image from each of the new images, and retrieves a region with the highest similarity from the extracted candidate regions of the stent marker, to detect coordinates of the stent marker.

When coordinates of the stent marker are detected from the sequentially generated X-ray images, the detection function 213 first identifies (specifies) the stent marker using a plurality of X-ray images. Specifically, the detection function 213 specifies the certain target object inserted into the body of the subject and drawn on the X-ray images using the sequentially generated X-ray image group, and detects coordinates of the certain target object included in a newly generated X-ray image on the basis of the specified results. For example, the detection function 273 extracts all the regions similar to the stent marker, for each of X-ray images in a predetermined period, using the stent marker designated by the operator or the stent marker based on the teacher image. Thereafter, the detection function 213 extracts a region with the highest likelihood of being the stent marker comprehensively from the regions extracted from the respective X-ray images, as the stent marker. The processing of detecting and identifying (specifying) the stent marker as described above will be referred to as "learning mode" hereinafter.

FIG. 3 is a diagram for explaining an example of the learning mode according to the first embodiment. FIG. 3 illustrates a learning mode using X-ray images of n frames generated with the image processing circuitry 26. For example, the detection function 213 extracts all the regions (coordinates) similar to the stent markers in all the regions of the first frame illustrated in FIG. 3. Thereafter, the detection function 213 forms pairs with all the extracted coordinates, and provides each of the pairs with evaluation points based on similarity and a distance between the coordinates. For example, the detection function 213 provides the pair of coordinates 51 and coordinates 52 with evaluation points. FIG. 3 illustrates only the coordinates 51 and the coordinates 52; however, when the image includes any region (coordinates) similar to the stent markers, these coordinates are also detected, and a pair is formed with the coordinates 51, the coordinates 52, or other coordinates, and provided with evaluation points.

In the same manner, the detection function 213 executes the processing described above for the second frame to the nth frames, and provides each of the pairs based on all the extracted coordinates with evaluation points. In addition, the detection function 213 extracts the coordinates of the pair indicating the highest evaluation points in each of the frames as the coordinates of the stent markers, and extracts a region including the coordinates that the stent markers can take in the X-ray images of the predetermined period. For example, as illustrated in FIG. 3, the detection function 213 extracts the pair of the coordinates 51 and the coordinates 52 indicating the highest evaluation points in each of the frames, and extracts the region including these coordinates.

For example, because the heartbeats and expansion and contraction of the lungs are regular (periodical), the stent markers moving with them exhibits regular (periodical) movement. In the learning mode described above, stent markers moving regularly (periodically) are comprehensively detected using X-ray images of the predetermined period, and identify (specify) one with the highest likelihood of being the stent marker, as the stent marker. In the learning mode, for example, X-ray images of approximately 40 frames are used.

As described above, first, the detection function 213 identifies (specifies) the stent markers in the X-ray image by the learning mode, to extract regions including coordinates that the stent markers can take. The detection function 213 detects the stent markers with the extracted regions serving as the center, to improve the detection accuracy.

Figure 4A:
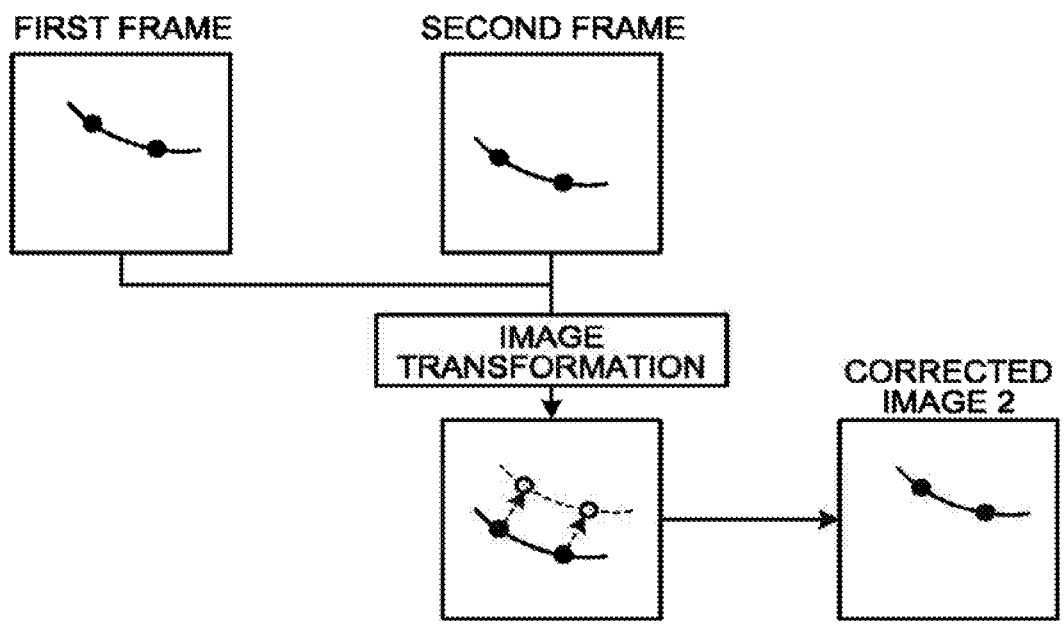
FIG. 4A is a diagram for explaining processing with a corrected image generation function according to the first embodiment.
Figure 4B:
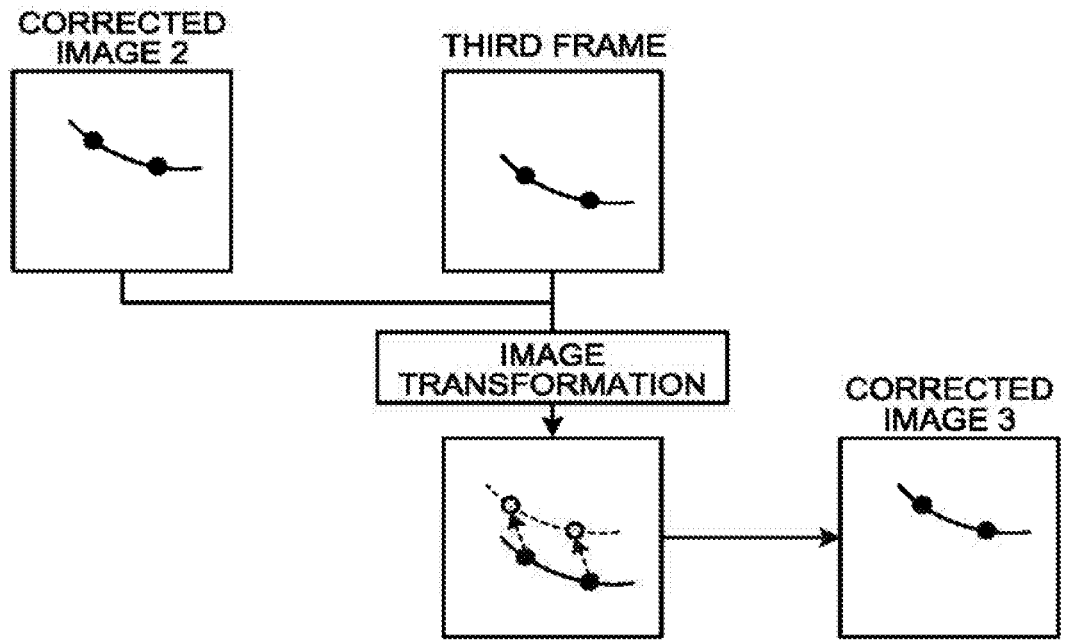
FIG. 4B is a diagram for explaining processing with a corrected image generation function according to the first embodiment.

The corrected image generation function 214 controls the image processing circuitry 25, to perform image transformation processing, such as affine transformation, on a new image such that the coordinates of the stent markers detected with the detection function 213 in the new image agree with reference coordinates, with the coordinates of the stent markers already detected with the detection function 213 serving as the reference coordinates, and generate a corrected image. The image transformation processing herein includes processing excluding expansion and contraction of the image, and includes processing only formed of image movement processing, such as parallel movement and turning movement. FIG. 4A and FIG. 4B are diagrams for explaining the processing with the corrected image generation function 214 according to the first embodiment. FIG. 4 and FIG. 4B illustrate processing on a new image in which coordinates of the stent markers are detected on the basis of the processing result of the learning mode, after processing in the learning mode with the detection function 213 is finished. Specifically, the first frame illustrated in FIG. 4A indicates an X-ray image generated first after the learning mode is finished.

For example, first, the detection function 213 executes processing in the learning mode using images of 40 frames, and detects coordinates of the stent markers using the processing result of the learning mode, for the first frame and the second frame generated after the learning mode is finished, as illustrated in FIG. 4A. For example, the detection function 213 extracts regions similar to the stent markers mainly from the regions extracted by the learning mode, and detects regions with the highest likelihood of being the stent markers, as the stent markers.

When the coordinates of the stent markers are detected with the detection function 213, the corrected image generation function 214 generates a corrected image 2 from the second frame by image transformation such that the coordinates of the stent markers detected in the X-ray image of the second frame generated as a new image agree with the coordinates (reference positions) of the stent markers already detected in the first frame, as illustrated in FIG. 4A. Thereafter, the corrected image generation function 214 generates a corrected image for each of new images of the third frame and the subsequent frames, using the coordinates of the stent markers in the corrected image generated with the function itself from the X-ray image generated directly before the new image as the reference coordinates. For example, as illustrated in FIG. 4B, the corrected image generation function 214 generates a corrected image 3 by image transformation from the third frame such that the coordinates of the stent markers detected in the third frame agree with the coordinates of the stent markers in the corrected image 2 generated from the second frame.

The present embodiment illustrates the case of using the coordinates of the stent markers in the corrected image generated from the previous frame of the new image as the reference coordinates, but the embodiments are not limited thereto. The coordinates of the stent markers detected in the first frame may be fixed as the reference coordinates, to generate a correct image from each of new images of the second frame and the subsequent frames. However, as described later, because a corrected image is used for generating a display image used for displaying a moving image, a corrected image may be generated from the new image using the previous corrected image.

As described above, the corrected image generation function 214 generates corrected images in which the coordinates of the stent markers detected with the detection function 213 agree between the images. Specifically, the corrected image generation function 214 generates corrected images in which coordinates of the stent markers detected from subsequent X-ray images using the processing result of the learning mode agree between the images, after the stent markers are identified by the learning mode. The processing of generating corrected image described above will be referred to as "tracking mode" hereinafter.

Figure 5:
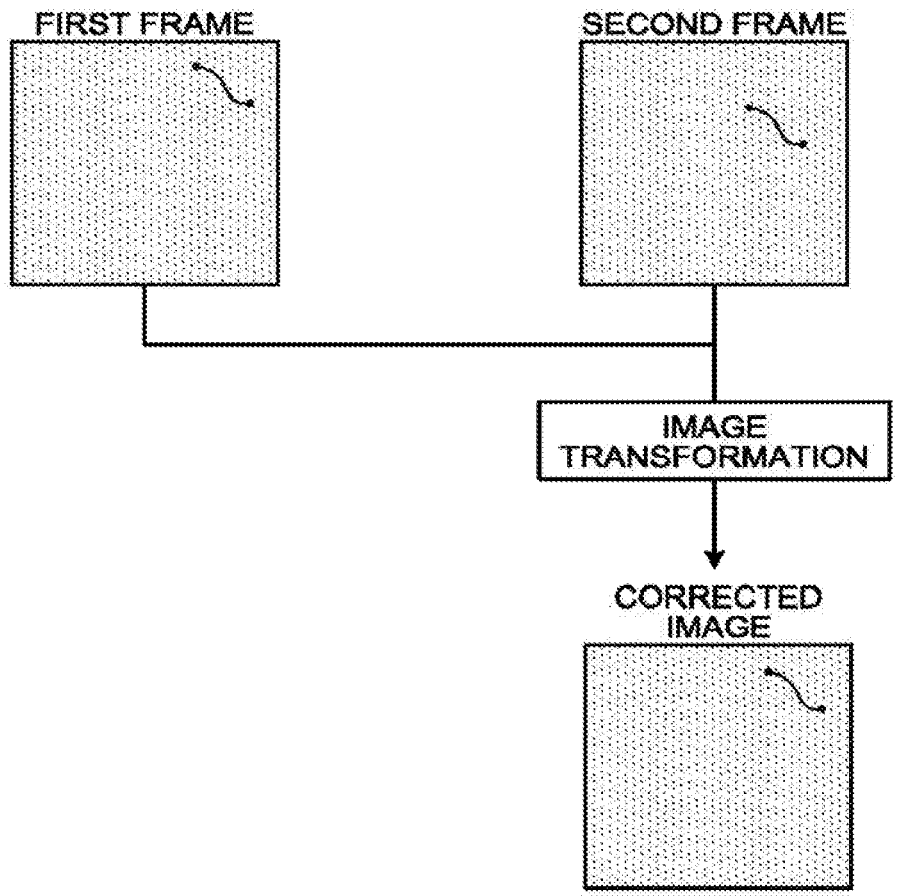
FIG. 5 is a diagram for explaining an example of a tracking mode according to the first embodiment.

FIG. 5 is a diagram for explaining an example of the tracking mode according to the first embodiment. For example, in the tracking mode, a corrected image is generated, as illustrated in FIG. 5. The corrected image is obtained by performing image transformation to cause the coordinates of the stent markers detected using the region extracted by the learning mode as the center to agree. Specifically, the corrected image generation function 214 generates a corrected image for the X-ray image for which the detection function 213 has detected the stent markers after the learning mode.

The display control function 215 displays the corrected images generated with the corrected image generation function 214 on the display 23, as a moving image. Specifically, whenever a corrected image is newly generated along the time series, the display control function 215 performs control to sequentially display the newly generated corrected images on the display 23, as display images. Specifically, the display control function 215 performs control to display the display images between which the coordinates of the stent markers agree with each other, as a moving image. This structure enables display of the X-ray images as a moving image in a state in which the stent portion does not move, for example, although the background portion other than the stent is blurred.

The display control function 215 controls the image processing circuitry 26, to display the display images obtained by performing various types of filter processing on the corrected images, as the moving image. For example, the display control function 215 controls the image processing circuitry 26, to execute high-frequency noise reduction filtering processing on the corrected images using a recursive filter, and generate the display images. The recursive filter is a filter of reducing high-frequency noise by adding pixel values of pixels forming the past frame subjected to predetermined weighting to the pixel values of the pixels forming the frame serving as the processing target. Because the coordinates of the stent markers agree in the corrected images, a recursive filter using the past frame also enables reduction in high-frequency noise of the stent portion and improvement in visibility of the stent in the corrected image. It suffices that the predetermined weighting in the recursive filter is determined at the point in time when filtering processing is performed. The predetermined weighting is determined before generation of the corrected image, during generation of the corrected image, or after generation of the corrected image.

Specifically, the display control function 215 causes successive execution of processing with the recursive filter using the past corrected images for sequentially generated corrected images, to generate display images with improved visibility of the device, and perform display of a moving image. The display control function 215 also enables generation of display images by simply adding the sequentially generated corrected images.

The processing in the display of a moving image in which the device looks as if the device is stationary has been described above. The example described above illustrates the case of performing image transformation such that the positions of the two stent markers of a newly generated X-ray image agree with the positions of the two stent markers of the X-ray image of the first frame. However, the embodiments are not limited thereto, and a corrected image may be generated using one point based on the two stent markers. Specifically, the detection function 213 executes processing of the learning mode for the coordinates of the two stent markers, to detect the two stent markers in the new image. The corrected image generation function 214 extracts one point (for example, the middle point of the two stent markers) based on the detected two stent markers, and generates a corrected image corrected to cause the extracted one point based on the stent markers to agree.

In such cases, the corrected image generation function 214 uses one point and an angle determined from the feature pattern detected in the X-ray image (for example, the first frame) set as the reference image. In addition, the corrected image generation function 214 generates a corrected image from the target image on the basis of the feature pattern detected in the target image serving as the X-ray image serving as the correction target, the predetermined one point, and the predetermined angle. The display control function 215 displays corrected images sequentially generated with the corrected image generation function 214 on the display 23, as a moving image. It suffices that the predetermined one point and the predetermined angle used for generation of the corrected image are determined at the point in time when the corrected image is generated. The point and the angle are determined before generation of the image data group, during generation of the image data group, or after generation of the image data group.

The following is an explanation of processing (one-point fixing processing) in the display of a moving image in which the device virtually looks as if the device is stationary using one point in the X-ray image. The following explanation illustrates the case where the treatment tool includes two feature points (for example, two stent markers). In such a case, the detection function 213 detects the two feature points of the tool, as the feature pattern. The corrected image generation function 214 uses one point determined with the coordinates of the two feature points detected in the reference image, as the predetermined one point. The corrected image generation function 214 also uses the angle between a line segment connecting the two feature points detected in the reference image and a reference line in the reference image, as the predetermined angle.

Figure 6:
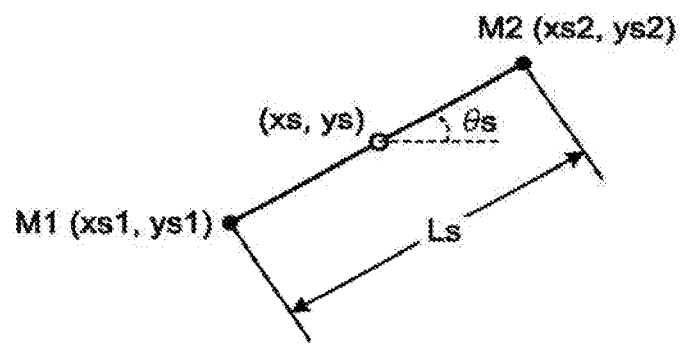
FIG. 6 is a diagram for explaining one-point fixing processing according to the first embodiment.

FIG. 6 is a diagram for explaining one-point fixing processing according to the first embodiment. For example, the detection function 213 detects coordinates of the respective two markers (M1 and M2), in the X-ray image of the first frame set as the reference image. As an example, as illustrated in FIG. 6, the detection function 213 detects "(xs1, ys1) and (xs2, ys2)", as coordinates of M1 and M2. From the detection result of the detection function 213, the corrected image generation function 214 determines "coordinates of one point" used for image transformation. For example, as illustrated in FIG. 6, the corrected image generation function 214 calculates the center coordinates "(xs, ys)" of M1 and M2. The center coordinates are the middle point of the line segment (hereinafter referred to as "line segment M1&2" connecting M1 with M2. Specifically, "as" is "(xs1+xs2)/2", and "vs" is "(ys1+ys2)/2". In addition, for example, the corrected image generation function 214 calculates the angle "θs" between the line segment M1&2 and the reference line in the horizontal direction of the reference image, as illustrated in FIG. 6.

In this manner, the "one point and angle" used for image transformation processing are determined. Thereafter, the detection function 213 detects the coordinates of M1 and M2 in the X-ray image (target image) serving as the correction target and generated after the reference image. The corrected image generation function 214 performs image transformation on the target image such that the middle point of the line segment M1&2 in the target image has coordinates (xs, ys) and the angle between the line segment M1&2 and the reference line is "θs". Specifically, in one-point fixing processing, image transformation is performed on the target image such that the device drawn on the corrected images extends through the same point and the inclination of the device drawn on corrected images has the same angle. The display control function 215 displays the corrected images sequentially generated with the corrected image generation function 214 on the display 23, as a moving image.

The processing in the display of a moving image in which the device virtually looks as if the device is stationary has been explained above. The X-ray diagnostic apparatus 100 according to the present application improves the image quality of the image in the display of a moving image in which the device virtually looks as if the device is stationary. As described above, in the display of a moving image in which the device virtually looks as if the device is stationary, the feature points (such as stent markers) in the device included in the X-ray image are detected, and the positions of the detected feature points are caused to substantially agree, in order to virtually stop the movement of the device. Specifically, the image quality of the moving image varies in accordance with the accuracy of detection of the feature points, the positions of which are caused to agree between the images. For example, when the detection function 213 detects (erroneously detects) a region similar to the stent marker as the stent marker, the corrected image generation function 214 generates a corrected image obtained by causing the erroneously detected region to agree with the stent marker. As a result, the moving image displayed on the display 23 is not an image in which the device virtually looks as if the device is stationary, and the image quality deteriorates.

For this reason, the X-ray diagnostic apparatus 100 according to the first embodiment improves the accuracy of detection of feature points (such as stent markers), the positions of which are caused to agree between the images, to improve the image quality. Specifically, when stent markers are detected, the X-ray diagnostic apparatus 100 excludes fixed objects included in the X-ray image from the target of detection, to improve the accuracy of detection of the stent markers and improve the image quality.

As described above, in the X-ray diagnostic apparatus 100, all the regions similar to the stent markers and included in the X-ray image are extracted, and regions with the highest likelihood of being the stent markers in the extracted regions is detected as the stent markers. The X-ray images to display a moving image in which the device is virtually stopped include regions moving by pulsation or the like in the same manner as the stent markers, and fixed regions, as regions similar to the stent markers. For example, the catheter in the aorta and the bones are not influenced by pulsation, and the positions thereof do not change between X-ray images chronologically collected, in many cases. In such objects with unchanged positions, a region having a pattern (features of the shape and the luminance) similar to the stent markers is detected as a candidate for the stent markers. Because the position of such a region does not change, the region tends to have clear contrast, and is easily erroneously detected as a region with highest likelihood of being the stent marker.

For this reason, the X-ray diagnostic apparatus 100 excludes regions of objects with unchanged positions and similar to the stent markers as described above from the target of detection of the stent markers, to improve the accuracy of detection of the stent markers. In the following explanation, a region of an object with unchanged position and similar to the stent marker is also referred to as fixed object. The following is an explanation of detailed processing of the X-ray diagnostic apparatus 100 according to the first embodiment.

Figure 7:
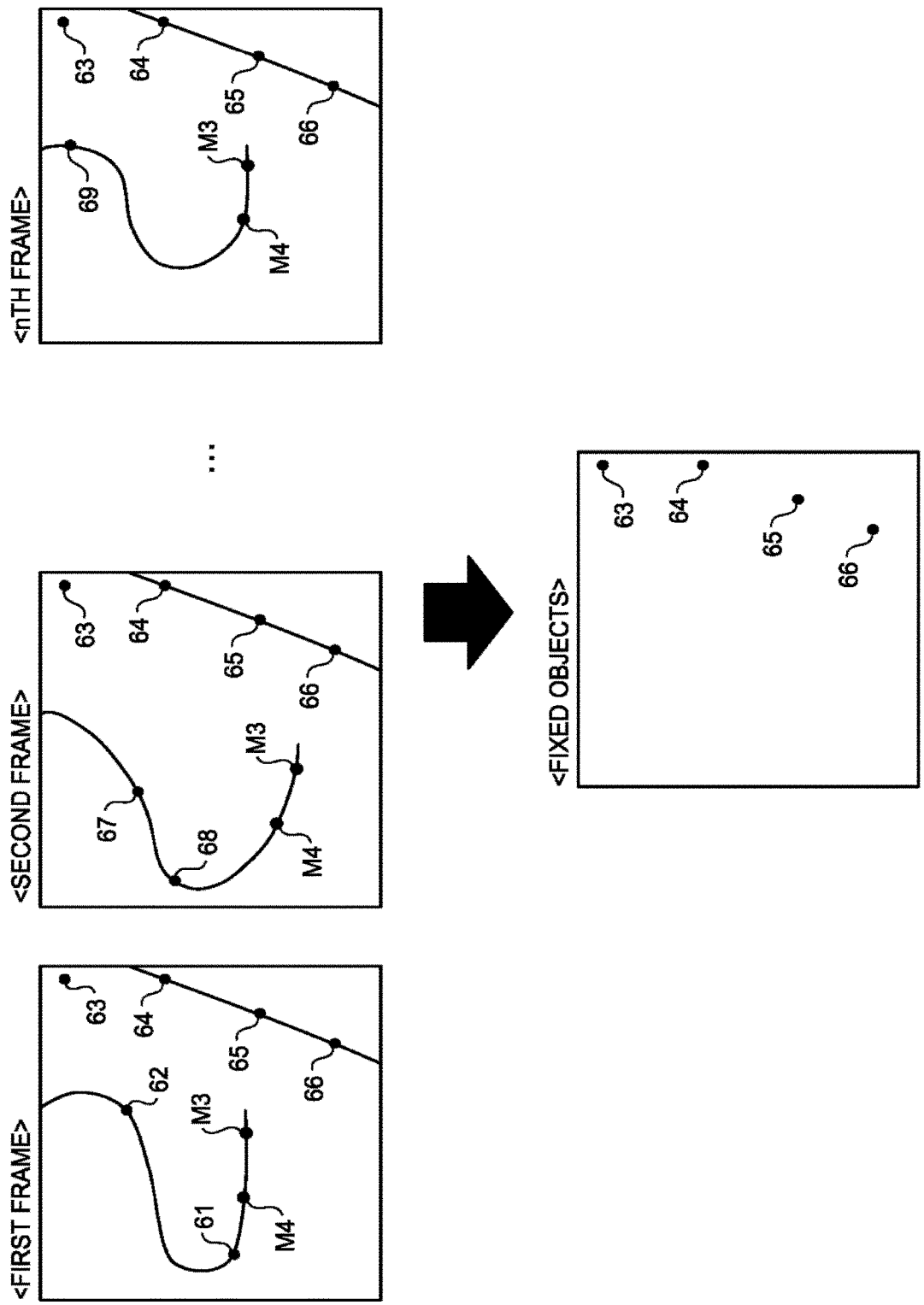
FIG. 7 is a diagram for explaining an example of processing of extracting fixed objects with an extraction function according to the first embodiment.

The extraction function 212 according to the first embodiment extracts fixed objects included in X-ray images chronologically collected. Specifically, the extraction function 212 extracts a drawn object drawn in almost the same position in the X-ray images, as a fixed object. More specifically, the extraction function 212 extracts a region similar to the stent markers in an object with unchanged position from the X-ray images, prior to detection of the stent markers. FIG. 7 is a diagram for explaining an example of processing of extracting fixed objects with the extraction function 212 according to the first embodiment. For example, as illustrated in FIG. 7, the extraction function 212 extracts fixed objects using the nth frame from the first frame chronologically collected. The frame serving as a target of extraction of fixed objects with the extraction function 212 may be a frame of any timing. Specifically, the extraction function 212 is capable of extracting fixed objects for frames in the learning mode and frames in the tracking mode.

For example, as illustrated in FIG. 7, the extraction function 212 extracts region M3, region M4, and regions 61 to 66, as regions similar to the stent markers, in the first frame. As an example, the extraction function 212 generates a frequency image in which the stent markers are highlighted in the same manner as the detection function 213 described above, to extracts the region M3, the region M4, and the regions 61 to 66, as regions similar to the stent markers. As illustrated in FIG. 7, because all the regions similar to the stent markers are extracted, the regions 61 to 66 are extracted, as well as the regions M3 and M4 being the actual stent marker regions. In the same manner, the extraction function 212 extracts the region M3, the region M4, and regions 63 to 66, as regions similar to the stent markers, in the second frame. In the same manner, the extraction function 212 extracts the region M3, the region M4, regions 63 to 66, and a region 69, as regions similar to the stent markers, in the nth frame.

As described above, the extraction function 212 extracts all the regions similar to the stent markers, for each of the frames sequentially collected. Thereafter, the extraction function 212 extracts regions having unchanged positions between the frames, as fixed objects. Specifically, the extraction function 212 extracts drawn objects drawn in almost the same positions in a plurality of frames, as fixed objects. For example, as illustrated in FIG. 7, because the positions of the regions 63 to 66 do not change, the extraction function 212 extracts the regions as fixed objects. Determination of change in position of a region is performed by, for example, addition processing of frames. For example, the extraction function 212 adds the first to the nth frames, and determines a region having a luminance value exceeding a predetermined threshold, as a region having an unchanged position. The regions M3 and M4 serving as actual stent marker regions are not extracted as fixed objects, because the positions of the regions change by pulsation or the like. It suffices that the predetermined threshold used for determination of change in position of a region is determined at the point in time when the determination processing is performed. For example, the predetermined threshold is determined before generation of the image data group, during generation of the image data group, or after generation of the image data group.

The extraction function 212 performs extraction of fixed objects described above, whenever an X-ray image is collected. For example, when radioscopy is started, the extraction function 212 extracts all the regions similar to the stent markers in the collected frame. The extraction function 212 sequentially extracts all the regions similar to the stent markers, for each of the frames sequentially collected. Thereafter, when the extraction function 212 extracts all the regions similar to the stent markers for each of the frames to the nth frames from the start of collection, the extraction function 212 executes the processing of extracting fixed objects as described above using the first to the nth frames. Thereafter, the extraction function 212 transmits information of the extracted fixed objects to the detection function 213. For example, the extraction function 212 transmits coordinate information of the extracted fixed objects to the detection function 213.

In addition, the extraction function 212 is also capable of extracting regions similar to the stent markers for each of frames sequentially collected after the nth frame, to continue the processing of extracting fixed objects. In such a case, for example, the extraction function 212 extracts fixed objects using the past X-ray image group within a certain period from an X-ray image from which fixed objects have been newly extracted. As an example, when the (n+1)th frame is collected, the extraction function 212 executes the processing of extracting fixed objects described above using the frames from the second frame to the (n+1)th frame. As described above, the extraction function 212 extracts fixed objects using the past frames within a predetermined period from the current frame, to enable accurate extraction of the positions of fixed objects, even when the position of the image to be imaged is changed during radioscopy. The extraction function 212 sequentially transmits information of the fixed objects extracted as described above to the detection function 213.

The extraction function 212 is capable of transmitting information of the fixed objects as an image to the detection function 213. Specifically, the extraction function 212 generates a fixed object image illustrating the extracted fixed objects, and transmits the generated fixed object image to the detection function 213. For example, the extraction function 212 generates a fixed object image in which fixed objects are drawn using the frame in which the fixed objects are extracted. As an example, the extraction function 212 transmits an addition image obtained by adding the frame to determine whether the positions of the regions similar to the stent markers have changed (whether the regions are fixed objects), as the fixed object image, to the detection function 213.

The extraction function 212 is also capable of updating the fixed object image using sequentially generated frames. For example, the extraction function 212 updates the fixed object image, by sequentially adding sequentially generated frames to the fixed object image. The extraction function 212 is also capable of generating a fixed object image using frames of the predetermined period. As an example, the extraction function 212 generates a fixed object image using the first to the nth frames. Thereafter, when the (n+1)th frame is generated, the extraction function 212 updates the fixed object image to a fixed object image using the second to the (n+1)th frames. As described above, the extraction function 212 is capable of sequentially updating the fixed object image in accordance with collection of frames.

The extraction function 212 is also capable of updating the fixed object image in accordance with extraction results of fixed objects. For example, the extraction function 212 extracts fixed objects whenever a frame is collected, and updates the fixed object image when the positions of the extracted fixed objects change from the previous positions of the fixed objects. Thereafter, the extraction function 212 transmits the updated fixed object image to the detection function 213. The processing of the extraction function 212 according to the first embodiment has been described above. The number "n" serving as the number of frames described above can be set to any number.

The detection function 213 according to the first embodiment detects target objects included in the X-ray images, excluding the fixed objects included in the X-ray images from the target of detection. Specifically, when the detection function 213 detects the target objects (for example, the stent markers), the detection function 213 performs processing of detecting target objects, after excluding the fixed objects extracted with the extraction function 212 from candidates for the target objects. For example, first, the detection function 213 extracts regions similar to the stunt markers in the frame, as described above. Thereafter, the detection function 213 excludes the regions of fixed objects from the extracted regions, on the basis of coordinate information of the fixed objects received from the extraction function 212, and detects the regions with the highest likelihood of being the stent markers from the remaining regions.

The detection processing described above can be performed at any timing after the extraction function 212 extracts fixed objects. For example, when the detection function 213 performs processing in the learning mode simultaneously with the start of radioscopy, the extraction function 212 performs the processing of extracting fixed objects, simultaneously with the learning mode with the detection function 213. Specifically, from the start of radioscopy until collection of the nth frame, the detection function 213 detects the stent markers, with all the regions including fixed objects as candidates for the stent markers. Thereafter, then the nth frame is collected and fixed objects are extracted, the detection function 213 specifies regions excluded from the targets of detection of the stent markers on the basis of coordinate information of the fixed object received from the extraction function 212, and performs the processing of detecting the stent markers, with the regions other than the specified regions serving as candidates. The detection function 213 may perform processing in the learning mode after the extraction function 212 extracts fixed objects.

In addition, the detection function 213 continuously performs the processing of detecting the stent markers using coordinate information of the fixed objects received from the extraction function 212, also in the tracking mode after the learning mode is finished. This structure enables detection of the stent markers, excluding fixed objects from the targets, suppresses erroneous detection of the stent markers, and improves the image quality.

In addition, when the extraction function 212 sequentially updates and transmits information of the fixed objects, the detection function 213 performs the processing of detecting the stent markers using the latest fixed object information. For example, when the extraction function 212 sequentially updates and transmits coordinate information of the fixed objects, the detection function 213 performs the processing of detecting the stent markers using the latest coordinates of the fixed objects received from the extraction function 212.

Figure 8:
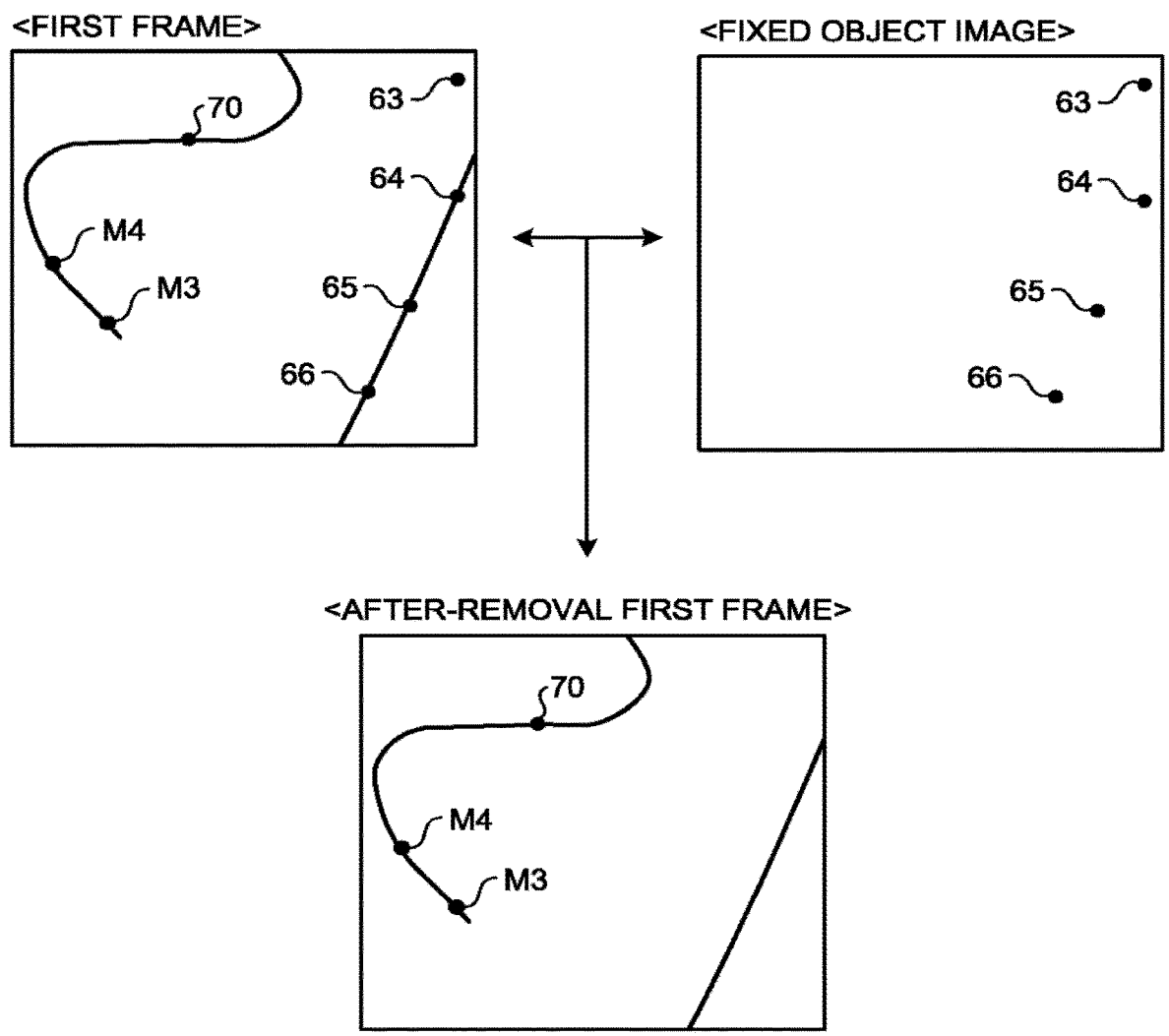

In addition, when the detection function 213 receives a fixed object image as information of the fixed objects, the detection function 213 removes fixed objects in each of the frames using the fixed object image, and thereafter extracts regions similar to the stent markers, to detect regions with the highest likelihood of being the stent markers from the extracted regions. FIG. 8 is a diagram for explaining an example of the detection processing with the detection function 213 according to the first embodiment. FIG. 8 illustrates processing in the case where the detection function 213 detects the stent markers from the first frame, and the first frame after the extraction function 212 generates a fixed object image serves as the first frame.

For example, as illustrated in FIG. 8, the first frame includes the region M3, the region M4, regions 63 to 66, and a region 70. Accordingly, when detection of the stent markers is performed in this state, all the regions are extracted as candidates for the stent markers. For this reason, the detection function 213 subtracts the fixed object image from the first frame illustrated in FIG. 6, to generate an after-removal first frame obtained by removing the fixed objects. Thereafter, the detection function 213 extracts the regions included in the after-removal first frame, candidates for the stent markers. Specifically, the detection function extracts the region M3, the region M4, and the region 70 included in the after-removal first frame, as candidates for the stent markers. Thereafter, the detection function 213 forms pairs with these regions, and provides each of the pairs with evaluation points on the basis of similarity and the like. Thereafter, the detection function 213 detects a pair with the highest evaluation points, as the stent markers. Specifically, the detection function 213 detects the region M3 and the region M4 as the stent markers. The detection function 213 performs the detection processing described above on each of the sequentially generated frames, to detect the stent markers in each of the frames.

As described above, the detection function 213 excludes fixed objects in the frame from candidates for the stent markers using information (such as coordinate information of the fixed object, and a fixed object image) of the fixed objects extracted with the extraction function 212, to perform detection processing, with the regions other than the fixed objects serving as candidates for the stent markers. When the fixed object image is sequentially updated and transmitted, the detection function 213 excludes the fixed objects in the frame from candidates for the stent markers using the latest fixed object image.

The corrected image generation function 4 generates corrected images in which the stent markers between the frames are caused to substantially agree on the basis of the detection result obtained with the detection function 213. For example, the corrected image generation function 214 sequentially generates corrected images obtained by correcting the respective frames to cause the positions of the region M3 and the region M4 to substantially agree in the sequentially generated frames. As an example, the corrected image generation function 214 generates corrected images from the respective frames to cause the positions of the region M3 and the region M4 to substantially agree in frames (frames in which fixed objects are not removed in detection of the stent markers) generated with the image processing circuitry 26. As another example, the corrected image generation function 214 generates corrected images from the respective frames to cause the positions of the region M3 and the region M4 to substantially agree in frames in which fixed objects are removed in detection of the stent markers.

Figure 9A:
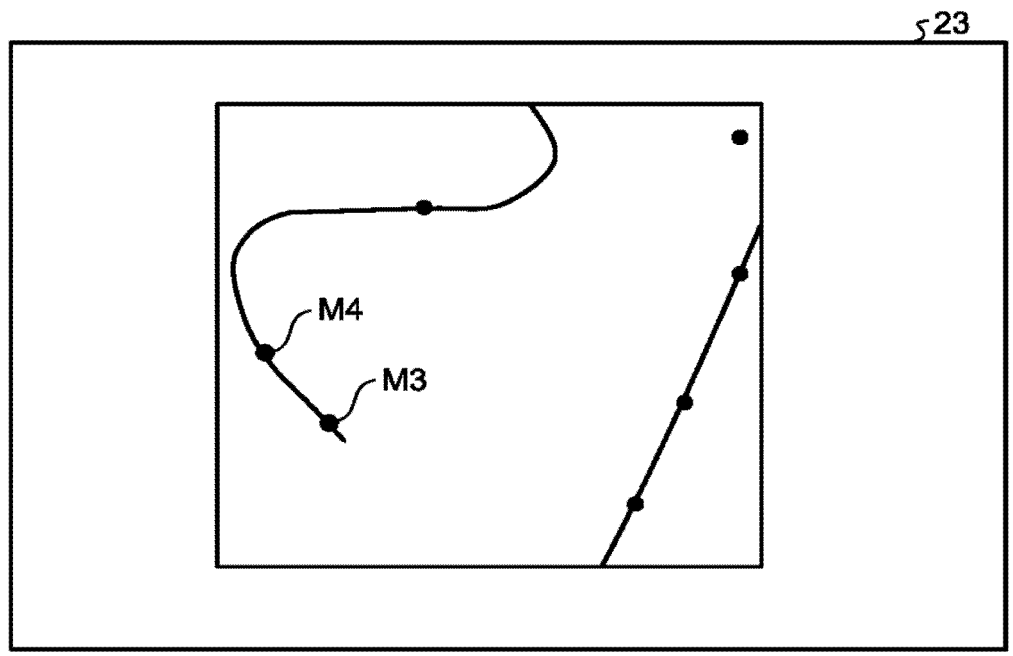
FIG. 9A is a diagram illustrating an example of a moving image displayed with a display control function according to the first embodiment.
Figure 9B:
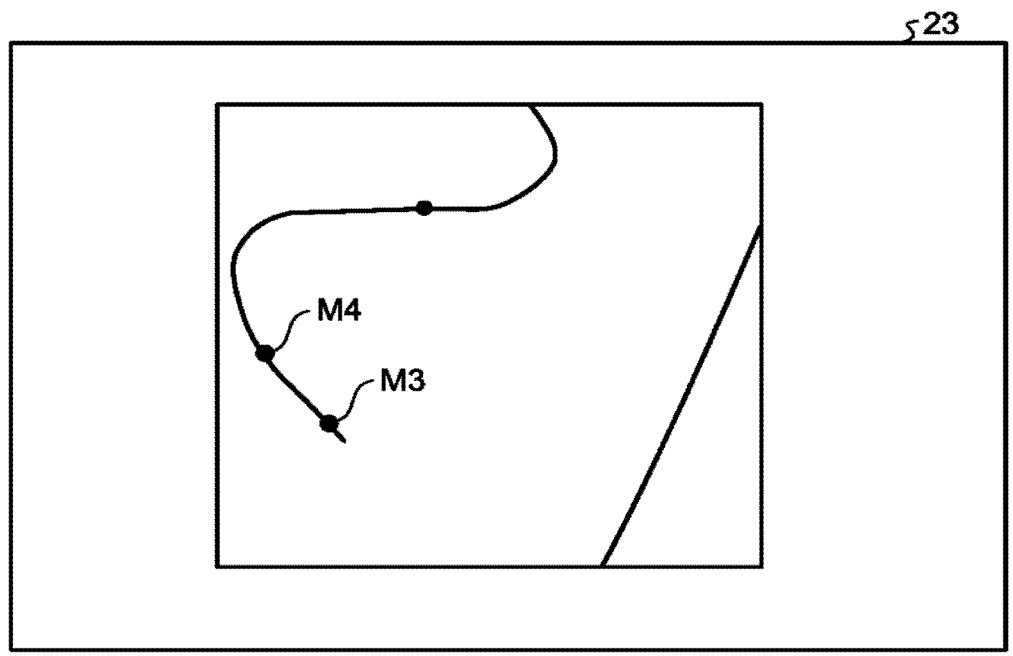
FIG. 9B is a diagram illustrating an example of a moving image displayed with the display control function according to the first embodiment.

The display control function 215 sequentially displays corrected images sequentially generated with the corrected image generation function 214 on the display 23. FIG. 9A and FIG. 9B are diagrams illustrating examples of a moving image displayed with the display control function 215 according to the first embodiment. FIG. 9A illustrates a moving image in the case where corrected images are generated from frames in which fixed objects are not removed in detection of the stent markers. FIG. 9B illustrates a moving image in the case where corrected images are generated from frames in which fixed objects are removed in detection of the stent markers.

For example, as illustrated in FIG. 9A, the display control function 215 sequentially displays corrected images generated from frames in which fixed objects are not removed, to display a moving image in which the two stent markers (region M3 and region M4) are virtually stationary. The display control function 215 may further improve the visibility of the stent by providing the corrected images with a recursive filter (by adding the past corrected images).

In addition, for example, as illustrated in FIG. 9B, the display control function 215 sequentially displays corrected images generated from frames in which fixed objects are removed, to display a moving image in which the two stent markers (region M3 and region M4) are virtually stationary. Because the moving image in FIG. 9B are based on corrected images in which fixed objects are removed, no fixed objects are illustrated in the moving image, and the moving image has higher visibility. The display control function 215 may further improve the visibility of the stent by providing the corrected images with a recursive filter (by adding the past corrected images).

Figure 10:
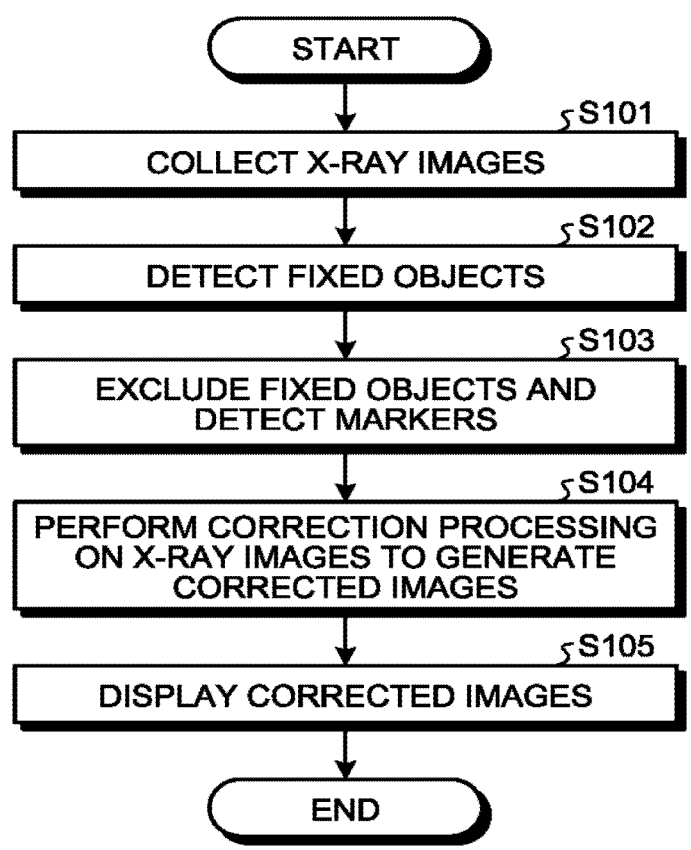
FIG. 10 is a flowchart illustrating a processing procedure of the X-ray diagnostic apparatus according to the first embodiment.

The following is an explanation of processing of the X-ray diagnostic apparatus 100 according to the first embodiment, with reference to FIG. 10. FIG. 10 is a flowchart illustrating a processing procedure of the X-ray diagnostic apparatus 100 according to the first embodiment. Step S101 illustrated in FIG. 10 is a step at which the processing circuitry 21 reads and executes a computer program corresponding to the control function 211 from the storage 25. Step S102 is a step at which the processing circuitry 21 reads and executes a computer program corresponding to the extraction function 212 from the storage 25. Step S103 is a step at which the processing circuitry 21 reads and executes a computer program corresponding to the detection function 213 from the storage 25. Step 2104 is a step at which the processing circuitry 21 reads and executes a computer program corresponding to the corrected image generation function 214 from the storage 25. Step S105 is a step at which the processing circuitry 21 reads and executes a computer program corresponding to the display control function 215 from the storage 25.

At Step S101, the processing circuitry 21 collects X-ray images. At Step S102, the processing circuitry 21 extracts fixed objects from the respective collected X-ray images. At Step S103, the processing circuitry 21 excludes the fixed objects from the respective X-ray images, to detect the respective markers. At Step 2104, the processing circuitry 21 performs image transformation on the respective X-ray images on the basis of the positions of the markers, to generate respective corrected images. At Step S105, the processing circuitry 21 sequentially displays the corrected images.

As described above, according to the first embodiment, the extraction function 212 extracts fixed objects included in a plurality of X-ray images chronologically collected. The detection function 213 detects target objects included in the respective X-ray images, excluding the fixed objects included in the X-ray images from the targets of detection. The corrected image generation function 214 sequentially generates corrected images obtained by performing correction processing to cause the positions of the target objects detected in the newly generated X-ray image to substantially agree with the reference positions. The reference positions are set to positions of the target objects detected in the reference image in the X-ray images. The display control function 215 sequentially displays the corrected images sequentially generated with the corrected image generation function 214 on the display 23. This structure enables the X-ray diagnostic apparatus 100 according to the first embodiment to suppress erroneous detection of detecting fixed objects, and improve the image quality in the display of a moving image in which the device virtually looks stationary.

In addition, according to the first embodiment, the extraction function 212 extracts fixed objects using a past X-ray image group within a preset period from an X-ray image in which fixed objects are newly extracted. This structure enables the X-ray diagnostic apparatus 100 according to the first embodiment to accurately extract fixed objects, and suppress erroneous detection, even when the imaging direction or the like is changed and the positions of the fixed objects are changed.

According to the first embodiment, the extraction function 212 generates a fixed object image illustrating fixed objects. The detection function 213 subtracts the fixed object image from each of the X-ray images, to remove the fixed objects from the X-ray images, and detect target objects from each of the X-ray images from which the fixed objects have been removed. This structure enables the X-ray diagnostic apparatus 100 according to the first embodiment to securely exclude fixed objects from the targets, and further suppress erroneous detection.

According to the first embodiment, the extraction function 212 generates the fixed object image using the X-ray images in which fixed objects are extracted. This structure enables the X-ray diagnostic apparatus 100 according to the first embodiment to use a fixed object image clearly illustrating fixed objects, and remove the fixed objects with accuracy.

According to the first embodiment, the extraction function 212 updates the fixed object image, in accordance with extraction results of the fixed objects. This structure enables the X-ray diagnostic apparatus 100 according to the first embodiment to reduce the processing load.

According to the first embodiment, the extraction function 212 extracts drawn objects drawn in substantially the same positions in the X-ray images, as the fixed objects. This structure enables the X-ray diagnostic apparatus 100 according to the first embodiment to extract fixed objects with accuracy.

According to the first embodiment, the display control function 215 displays corrected images in which the fixed objects are removed on the display 23. This structure enables the X-ray diagnostic apparatus 100 according to the first embodiment to display a moving image with high visibility.

According to the first embodiment, the display control function 215 displays an addition image obtained by adding corrected images in which the fixed objects are removed on the display 23. This structure enables the X-ray diagnostic apparatus 100 according to the first embodiment to display a moving image with higher visibility.

Second Embodiment

The first embodiment described above illustrates the case of detecting the stent markers, with the whole image serving as the target. The second embodiment illustrates the case of detecting the stent markers, with a predetermined region in the image serving as the target. The X-ray diagnostic apparatus 100 according to the second embodiment is different from that of the first embodiment, in details of processing performed with the extraction function 212, the detection function 213, and the display control function 215. The details of the processing will be mainly explained hereinafter. It suffices that the predetermined region serving as the target of detection of the stent markers is determined until the point in time when the detection processing is started. For example, the predetermined region is determined during generation of the image data group, or after generation of the image data group.

The extraction function 212 according to the second embodiment extracts fixed objects included in the predetermined region in a plurality of X-ray images. Specifically, the extraction function 212 extracts fixed objects included in a detection region in which target objects are detected, in a plurality of X-ray images. The detection function 213 according to the second embodiment detects respective target objects included in the detection region in a plurality of X-ray images, excluding the fixed objects extracted with the extraction function 212 from the targets of detection. Specifically, the extraction function 212 and the detection function 213 according to the second embodiment performs processing of extracting fixed objects and processing of detecting target objects, respectively, in a detection region for target objects (such as the stent markers). This structure enables the X-ray diagnostic apparatus 100 according to the second embodiment to reduce the processing load. The detection region is set with the detection function 213. For example, the detection function 213 set a range in which the target objects can move, as the detection region.

The detection region for the target objects can be determined automatically and manually. First, the following is an explanation of the case of automatically determining the detection region for the target objects. As described above, in the X-ray diagnostic apparatus 100, a region including the positions that the stent markers can take can be extracted by the learning mode. The extraction function 212 and the detection function 213 performs processing of extracting fixed objects and processing of detecting the target objects, respectively, on the region extracted by the learning mode.

Figure 11:
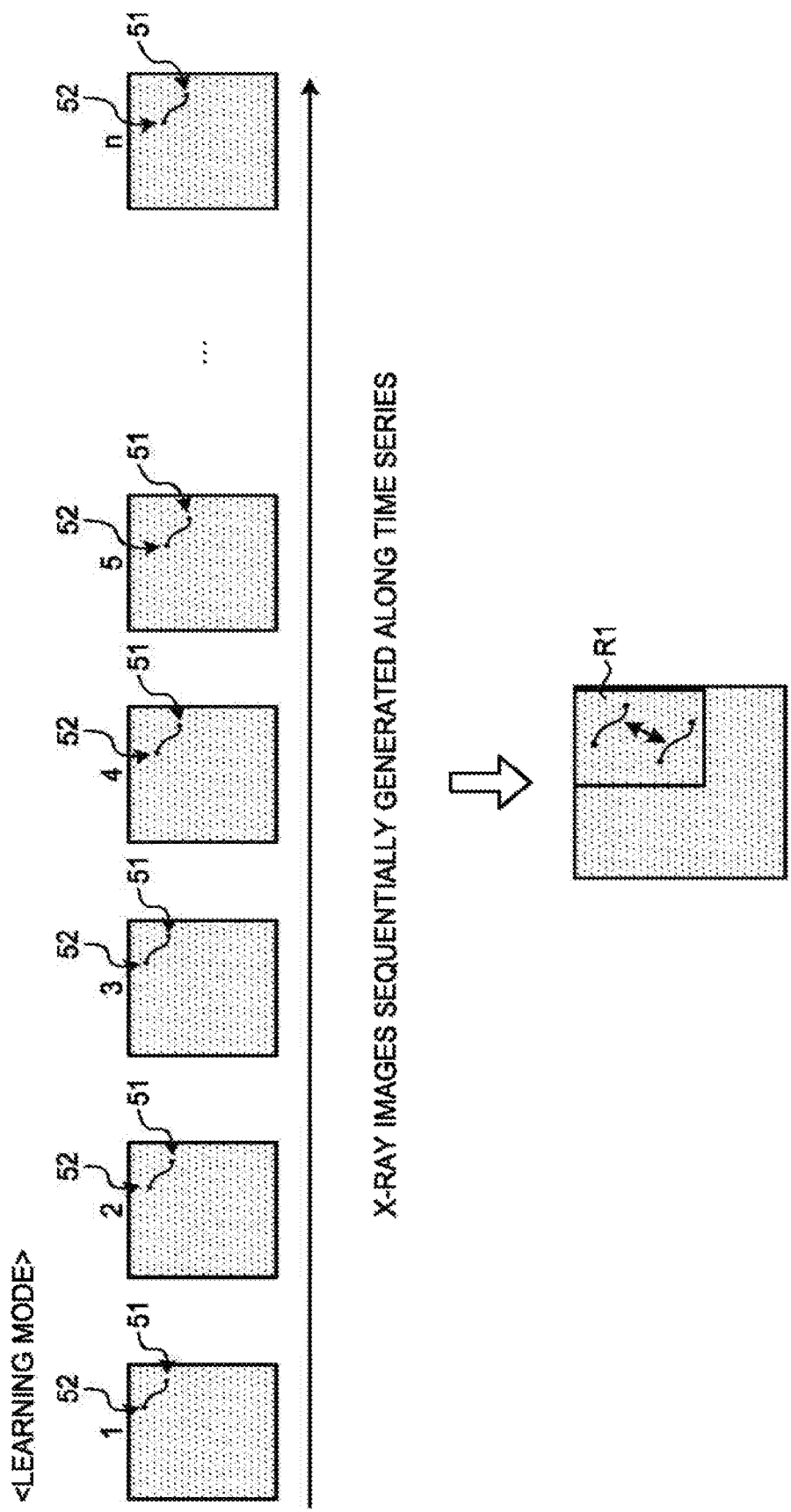
FIG. 11 is a diagram for explaining an example of region setting by the learning mode according to a second embodiment.

FIG. 11 is a diagram for explaining an example of setting of the region by the learning mode according to the second embodiment. For example, as illustrated in FIG. 11, the X-ray diagnostic apparatus 100 according to the second embodiment sets the region extracted by the learning mode as a region R1. Specifically, the detection function 213 in the X-ray diagnostic apparatus 100 sets the region R1 including the positions that the stent markers can take in X-ray images of a predetermined period, as the detection region serving as the target of the processing of extracting fixed objects and the processing of detecting the stent markers.

Figure 12:
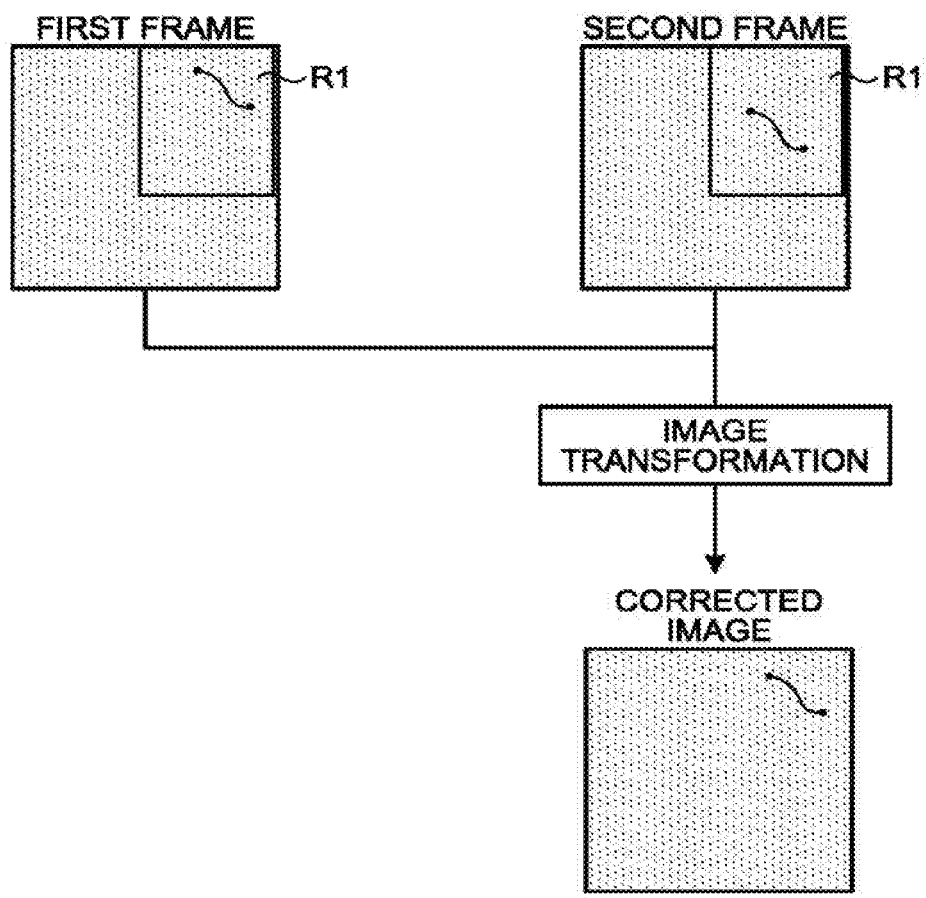
FIG. 12 is a diagram for explaining processing with the extraction function and the detection function according to the second embodiment.

The extraction function 212 and the detection function 213 perform processing of extracting fixed objects and processing of detecting the stent markers, respectively, on the set region. FIG. 12 is a diagram for explaining the processing with the extraction function 212 and the detection function 213 according to the second embodiment. For example, the extraction function 212 and the detection function 213 perform processing of extracting fixed objects and processing of detecting the stent markers, respectively on the region R1 illustrated in FIG. 12 and serving as the target.

The following is an explanation of the case of manually determining the detection region for the target objects. In such a case, the display control function 215 displays a GUI to set the detection region for the target objects on the display 23, together with the collected X-ray images. For example, the display control function 215 displays frames collected from the start of radioscopy as a moving image, and displays the region to set the detection region on the moving image.

Figure 13:
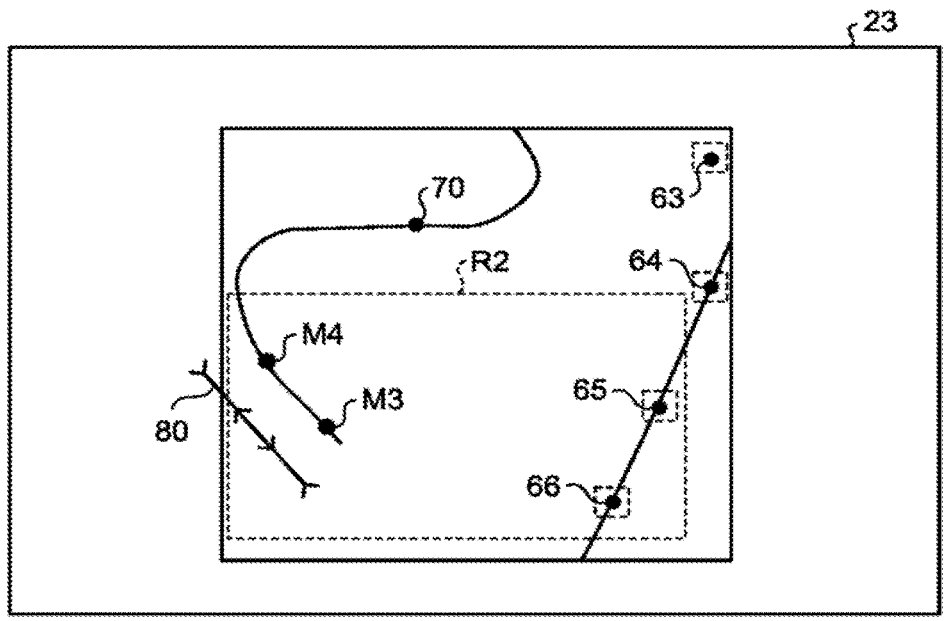
FIG. 13 is a diagram for illustrating an example of a region setting picture displayed with the display control function according to the second embodiment.

FIG. 13 is a diagram illustrating an example of a region setting picture displayed with the display control function 215 according to the second embodiment. For example, as illustrated in FIG. 13, the display control function 215 displays a region R2 to set a detection region on the moving image. The operator sets the shape and the size of the region R2, while observing the state in which the two stent markers (regions M3 and M4) move, with reference to the picture illustrated in FIG. 13. The detection function 213 sets the set region R2 as the detection region. The extraction function 212 and the detection function 213 perform processing of extracting fixed objects and processing of detecting the stent markers on the set region R2.

The example described above illustrates the case of performing processing of extracting fixed objects and processing of detecting the stent markers, but the embodiments are not limited thereto. For example, processing of extracting fixed objects may be performed on a region (such as the whole image) including portions outside the set region. For example, the extraction function 212 performs processing of extracting fixed objects on a region other than the region R1 in FIG. 12, and a region other than the region R2 in FIG. 13. This structure enables the X-ray diagnostic apparatus 100 to promptly remove fixed objects, even when the region serving as the target processing of detecting the stent markers is reset.

When extraction of fixed objects in the whole image has been finished, the display control function 215 further displays information indicating the positions of the fixed objects on the moving image. For example, when the extraction function 212 has extracted regions 63 to 66 in FIG. 13 as fixed objects, the display control function 215 displays rectangles enclosing the respective regions, as illustrated in FIG. 13. This structure enables the user to recognize that these regions have already been determined as fixed objects. Specifically, when the user set the region R2, the user can recognize that these regions are not erroneously detected, even when these regions are included in the region R2. Consequently, this structure removes the necessity for the user to set the region R2 such that the region other than the stent markers are excluded as much as possible, and enables the user to easily set the region to detect the stent markers. The example described above illustrates the case of displaying information indicating the positions of the fixed objects on the moving image, to enable recognition of the fixed objects. However, candidates for the markers may be displayed to be recognizable. In such a case, the display control function 215 displays information indicating the positions of candidates for the markers on the moving image, to make the fixed objects recognizable. As an example, the display control function 215 displays rectangles enclosing the region M3, the region M4, and the region 70 illustrated in FIG. 13.

In addition, the X-ray diagnostic apparatus 100 is capable of setting conditions for a distance between the two stent markers, as well as setting the region serving as the target of processing of detecting the stent markers. Specifically, the display control function 215 displays a display image obtained by illustrating information indicating the positions of fixed objects and information to set conditions for detection of the target objects the X-ray image, on the display 23. The distance between the two stent markers in the X-ray image roughly falls within a determined range, although the distance slightly changes according to the application direction of X-rays to the two stent markers. For this reason, the X-ray diagnostic apparatus 100 sets conditions for the distance between the two stent markers, as information assisting the processing of detecting the stent markers. This structure enables the X-ray diagnostic apparatus 100 to more efficiently perform the processing of detecting the stent markers. For example, the upper limit value and the lower limit value of the preset distance of the stent markers are set in advance, and the detection function 213 is enabled to detect the two stent markers on the basis of the upper limit value and the lower limit value of the preset distance.

In addition, for example, the display control function 215 displays a GUI 80 to set conditions for the distance between the two stent markers on the moving image, as illustrated in FIG. 13. The operator operates the GUI 80 to set the upper limit value and the lower limit value of the distance between the two stent markers, while observing the two stent markers (region M3 and region M4). For example, the operator sets the upper limit value of the distance between the markers, with the distance held between the outside arrows of the GUI 80. Specifically, the operator changes the distance held between the outside arrows of the GUI 80, to set the upper limit value of the distance between the markers to a desired value. In addition, for example, the operator sets the lower limit value of the distance between the markers, with the distance held between the inside arrows of the GUI 80. Specifically, the operator changes the distance held between the inside arrows of the GUI 80, to set the lower limit value of the distance between the markers to a desired value.

The GUI 80 illustrated in FIG. 13 is rotatable to change the direction thereof. For example, the operator can rotate the GUI 80 such that the GUI 80 extends along the direction of the line segment formed between the two stent markers (region M3 and region M4), to set the upper limit value and the lower limit value of tree distance after rotation. In this manner, the operator is enabled to easily set conditions for the distance in accordance with the stent markers illustrated in the X-ray image. As illustrated in FIG. 13, the GUI 80 may be used in a state of projecting to the outside of the display region of the X-ray image, as well as on the X-ray image.

The example described above illustrates the case of setting the region or the conditions for the distance on the moving image, but the embodiments are not limited thereto. The region or the conditions for the distance may be set on a stationary image. For example, the display control function 215 displays an X-ray image (last image hold: LIH image) generated last in the X-ray images sequentially generated along the time series, and the operator sets the region or the conditions for the distance for the displayed LIH image. The display control function 215 is also capable of displaying an X-ray image selected by the operator from the X-ray images sequentially generated along the time series, on the display 23. For example, the operator operates the input interface 22, to switch the X-ray image (stationary image) displayed on the display 23 to a desired X-ray image, and set the region or the conditions for the distance on the switched desired X-ray image. Specifically, the display control function 215 displays a display image on the display 23, and the display image is obtained by illustrating, on the second X-ray image, information indicating the positions of fixed objects and information to set conditions for detecting the target objects that are set on the first X-ray image.

The display control function 215 is also capable of switching the displayed X-ray images, while the set region or the conditions for the distance are maintained. Specifically, the display control function 215 switches only the X-ray images displayed on the display 23, in the state in which the set region or the GUI indicating the conditions for the distance are kept displayed on the display 23. For example, after the operator sets the region or the conditions for the distance, the operator operates the input interface 22 again to switch X-ray images, to determine whether the set region or the conditions for the distance are proper. In this manner, for example, when the X-ray images displayed by switching include any X-ray image in which the stent markers are located outside the set region, the operator can reset the region.

As described above, according to the second embodiment, the extraction function 12 extracts fixed objects included in the detection region for the target objects in a plurality of X-ray images. The detection function 213 excludes the fixed objects extracted with the extraction function 212 from the targets of detection, and detects the target objects included in the detection region in each of the X-ray images. This structure enables the X-ray diagnostic apparatus 100 according to the second embodiment to reduce the load of the processing to improve the image quality.

In addition, according to the second embodiment, the display control function 215 displays display images obtained by illustrating information indicating the positions of the fixed objects and information indicating the region serving as the target of detection for the target objects on the X-ray images, on the display 23. This structure enables the X-ray diagnostic apparatus 100 according to the second embodiment to easily set the region.

Third Embodiment

The first and the second embodiments have been described above, but various different forms may be carried out, besides the first and the second embodiments described above.

Figure 14:
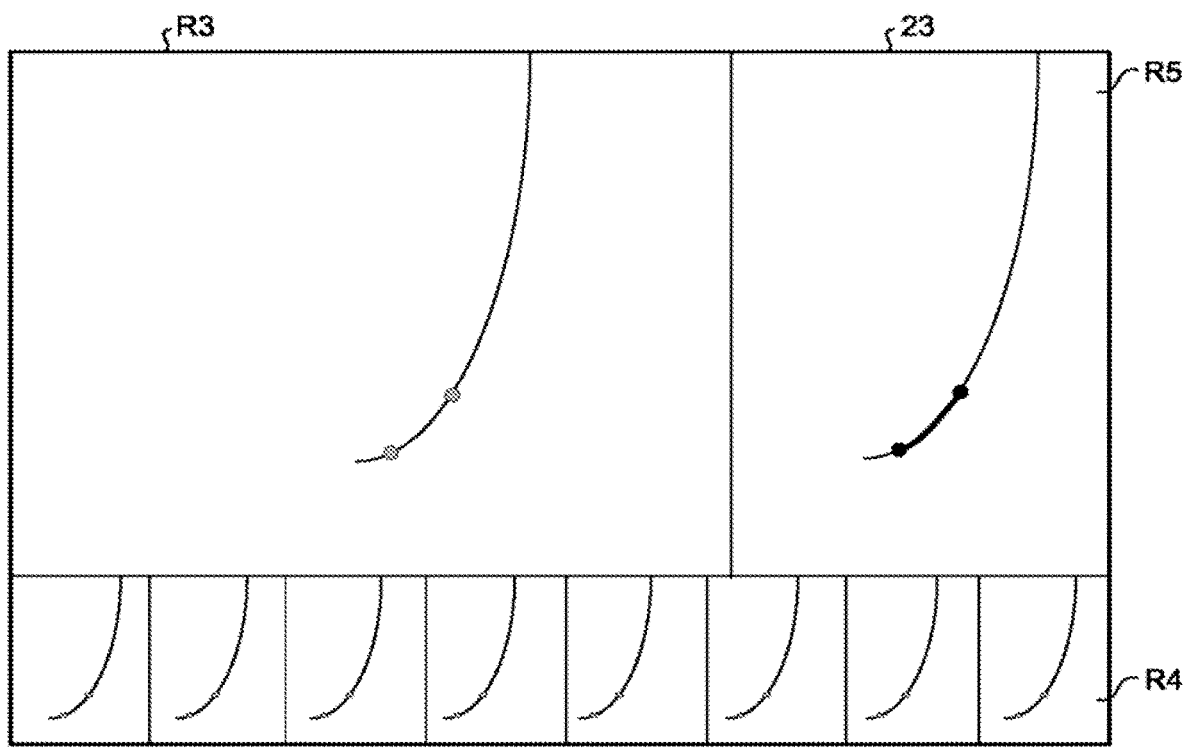
FIG. 14 is a diagram illustrating an example of image display with the display control function according to a third embodiment.

The embodiments described above illustrate display of a moving image in which fixed objects are not removed, display of a moving image in which fixed objects are removed, and display of a moving image obtained by adding corrected images. However, the embodiments are not limited thereto, and the display form may be set as desired. FIG. 14 is a diagram illustrating an example of image display with the display control function 215 according to the third embodiment. For example, as illustrated in FIG. 14, the display control function 215 is capable of dividing the display region of the display 23 into a region 3 to a region 5, to display various images in each of the regions. For example, the display control function 215 is capable of displaying a radioscopic live image in the region R3, displaying corrected images that are not subjected to addition in the region R4, and displaying a corrected image (addition image) having been subjected to addition in the region R5.

The display control function 215 is capable of displaying the image in each of the regions, with one of the image in which fixed objects are removed and the image in which fixed objects are not removed. Specifically, the display control function 215 is capable of displaying a live image in which fixed objects are removed or a live image in which fixed objects are not removed, in the region R3. The display control function 215 is also capable of displaying corrected images in which fixed objects are removed or corrected images in which fixed objects are not removed, in the region R4. The display control function 215 is also capable of displaying an addition image in which fixed objects are removed or an addition image in which fixed objects are not removed, in the region R5 The display control function 215 is capable of displaying these images in a desired combination.

The embodiments described above illustrate the case where the X-ray diagnostic apparatus 100 performs each of the processes. However, the embodiments are not limited thereto, and for example, an image processing apparatus may perform each of the processes. As an example, an image processing apparatus connected with the X-ray diagnostic apparatus 100 or an image storage apparatus and the like through a network acquires images through the network to perform the processing described above on the acquired images. Specifically, the processing circuitry in the image processing apparatus may perform the extraction function 212, the detection function 213, the corrected image generation function 214, and the display control function 215 as described above.

The constituent elements of the devices illustrated in the first embodiment are functional and conceptual elements, and are not necessarily physically configured as illustrated. Specifically, the specific form of distribution and integration of each of the devices is not limited to the illustrated form, but the whole or part of each of the devices may be configured to be distributed or integrated functionally or physically in desired units, in accordance with various loads and the state of use. In addition, all or desired part of each of the processing functions executed in each of the devices may be achieved with a CPU and a computer program analyzed and executed in the CPU, or as hardware by a wired logic.

In addition, the processing method explained in the embodiments described above can be achieved by executing a prepared control program with a computer, such as a personal computer and a workstation. The control program can be distributed through a network, such as the Internet. The control program may can also be recorded on a computer-readable recording medium, such as a hard disk, a flexible disk (ED), a CD-ROM, a MO, and a DVD, and executed by being read from the recording medium with a computer.

As described above, at least one embodiment enables improvement in image quality.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising:
processing circuitry configured to
extract a fixed object included in chronologically collected X-ray images and having a substantially fixed position,
detect a target object included in each of the X-ray images, excluding the fixed object included in each of the X-ray images from the target of detection, and
generate a plurality of corrected images by a correction process to substantially match, with a reference position, the detected position of the target object in an X-ray image other than a reference X-ray image, the reference position being the detected position of the target object in the reference X-ray image.

2. The image processing apparatus according to claim 1, wherein the processing circuitry is configured to
sequentially acquire X-ray images,
sequentially detect the target object in the sequentially acquired X-ray images, and
sequentially generate the corrected images by sequentially subjecting the X-ray images in which the target object has been detected to the correction process.

3. The image processing apparatus according to claim 2, wherein the processing circuitry is configured to extract the fixed object using a past X-ray image group of a preset number.

4. The image processing apparatus according to claim 2, wherein the processing circuitry is configured to
sequentially generate addition images obtained by adding a plurality of corrected images in a time series order from the corrected images sequentially generated, and
sequentially cause a display to display the generated addition images.

5. The image processing apparatus according to claim 1, further comprising:
a storage configured to store X-ray images therein, wherein
the processing circuitry is configured to
detect the target object in each of the X-ray images stored in the storage, and generate the corrected images by sequentially subjecting the X-ray images in which the target object has been detected to the correction process.

6. The image processing apparatus according to claim 5, wherein the processing circuitry is configured to
generate an addition image obtained by adding the corrected images, and
cause a display to display the generated addition image.

7. The image processing apparatus according to claim 6, wherein the processing circuitry is configured to cause the display to display the addition image obtained by adding the corrected images in which the fixed object has been removed.

8. The image processing apparatus according to claim 1, wherein the processing circuitry is configured to
generate a fixed object image illustrating the fixed object, and
remove the fixed object from the X-ray images by subtracting the fixed object image from each of the X-ray images, to detect the target object from each of the X-ray images from which the fixed object has been removed.

9. The image processing apparatus according to claim 8, wherein the processing circuitry is configured to generate the fixed object image using the X-ray images in which the fixed object has been extracted.

10. The image processing apparatus according to claim 8, wherein the processing circuitry is configured to update the fixed object image in accordance with extraction results of the fixed object.

11. The image processing apparatus according to claim 1, wherein the processing circuitry is configured to extract a drawn object drawn in a substantially equal position in the X-ray images, as the fixed object.

12. The image processing apparatus according to claim 1, wherein the processing circuitry is configured to cause a display to display the corrected images.

13. The image processing apparatus according to claim 12, wherein the processing circuitry is configured to cause the display to display the corrected images in which the fixed object has been removed.

14. The image processing apparatus according to claim 12, wherein the processing circuitry is configured to cause the display to display a display image, the display image being obtained by illustrating information indicating a position of the fixed object and information to set conditions for detection of the target object on a moving image based on the X-ray images.

15. The image processing apparatus according to claim 12, wherein the processing circuitry is configured to cause the display to display a display image, the display image being obtained by illustrating information indicating a position of the fixed object and information to set conditions for detection of the target object on the X-ray image.

16. The image processing apparatus according to claim 12, wherein the processing circuitry is configured to cause the display to display a display image, in accordance with an operation by an operator, the display image being obtained by illustrating information indicating a position of the fixed object and information to set conditions for detection of the target object that are set on a first X-ray image on a second X-ray image.

17. The image processing apparatus according to claim 1, wherein the processing circuitry is configured to
further set a detection region to detect the target object in the X-ray images,
extract the fixed object included in the detection region in the X-ray images, and
detect the target object included in the detection region in each of the X-ray images, excluding the fixed object included in each of the X-ray images from the target of detection.

18. An X-ray diagnostic apparatus comprising:
collection circuitry configured to sequentially collect X-ray images; and
the image processing apparatus according to claim 1.

19. An image processing method comprising:
extracting a fixed object included in chronologically collected X-ray images and having a substantially fixed position;
detecting a target object included in each of the X-ray images, excluding the fixed object included in each of the X-ray images from the target of detection; and
generating a plurality of corrected images by a correction process to substantially match, with a reference position, the detected position of the target object in an X-ray image other than a reference X-ray image, the reference position being the detected position of the target object in the reference X-ray image.

20. An image processing apparatus comprising:
processing circuitry configured to
extract a fixed object included in chronologically collected X-ray images and having a substantially fixed position,
detect a target object included in each of the X-ray images, excluding the fixed object included in each of the X-ray images from the target of detection,
generate a plurality of corrected images by a correction process to substantially match, with a reference position, the detected position of the target object in an X-ray image other than a reference X-ray image, the reference position being the detected position of the target object in the reference X-ray image, and
cause a display to display the corrected images in which the fixed object has been removed.

* * * * *